United States Patent [19]

Harnden et al.

[11] Patent Number: 5,166,198

[45] Date of Patent: Nov. 24, 1992

[54] ANTIVIRAL PHOSPHONYLALKOXY PURINES

[75] Inventors: Michael R. Harnden; David M. Duckworth; Halina T. Serafinowska, all of Epsom, England

[73] Assignee: Beecham p.l.c., Brentford, England

[21] Appl. No.: 500,718

[22] Filed: Mar. 28, 1990

[30] Foreign Application Priority Data

Mar. 30, 1989 [GB] United Kingdom ............... 8907173

[51] Int. Cl.$^5$ ............... A61K 31/675; C07F 9/6512; C07F 9/6524

[52] U.S. Cl. ............... 514/81; 544/244; 544/243; 544/229; 556/405; 548/415; 558/175; 558/189; 558/217

[58] Field of Search ............... 544/244; 514/81

[56] References Cited

U.S. PATENT DOCUMENTS

| | | | |
|---|---|---|---|
| 4,323,573 | 4/1982 | Schaeffer | 544/244 X |
| 4,755,516 | 7/1988 | Tolman et al. | 514/262 |
| 4,910,307 | 3/1990 | Wyatt | 544/276 |

FOREIGN PATENT DOCUMENTS

| | | | |
|---|---|---|---|
| 0242482 | 10/1987 | European Pat. Off. | |
| 0294069 | 12/1988 | European Pat. Off. | 544/277 |
| 0298601 | 1/1989 | European Pat. Off. | 544/277 |
| 0313289 | 4/1989 | European Pat. Off. | |
| 0319228 | 6/1989 | European Pat. Off. | 544/244 |
| 0353955 | 2/1990 | European Pat. Off. | 544/244 |

OTHER PUBLICATIONS

Streicher, et al., Chemica Scripta, vol. 26, pp. 179–183 (1986).

*Primary Examiner*—Diana G. Rivers
*Attorney, Agent, or Firm*—Hopgood, Calimafde, Kalil, Blaustein & Judlowe

[57] ABSTRACT

A compound of formula (I), or a pharmaceutically acceptable salt thereof:

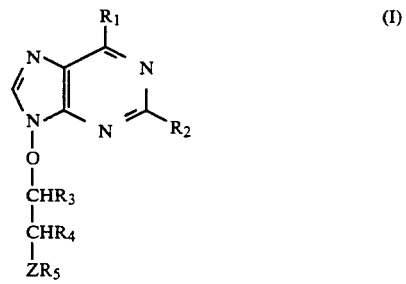

wherein
$R_1$ is hydroxy or amino;
$R_2$ is hydrogen or amino;
$R_3$ is hydrogen, hydroxymethyl or acyloxymethyl;
$R_4$ is hydrogen or (when $R_3=H$ and Z is a bond or $CH_2$) hydroxy, acyloxy, hydroxymethyl or acyloxymethyl;
Z is a bond, or a group $CHR_8$ wherein $R_8$ is hydrogen, or (when $R_3=R_4=H$), $R_8$ is hydroxy, acyloxy, hydroxymethyl or acyloxymethyl;
$R_5$ is a group of formula:

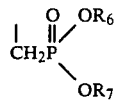

wherein
$R_6$ and $R_7$ are independently selected from hydrogen, $C_{1-6}$ alkyl and optionally substituted phenyl.

8 Claims, No Drawings

ANTIVIRAL PHOSPHONYLALKOXY PURINES

The present invention relates to compounds having antiviral activity, to processes for their preparation and to their use as pharmaceuticals.

EP-A-242482 (Beecham Group p.l.c.) describes a group of guanine derivatives having a 9-hydroxyalkoxy substituent, and possessing antiviral activity.

A novel, structurally distinct class of compounds has now been discovered, these compounds also having antiviral activity.

Accordingly, the present invention provides a compound of formula (I), or a pharmaceutically acceptable salt thereof:

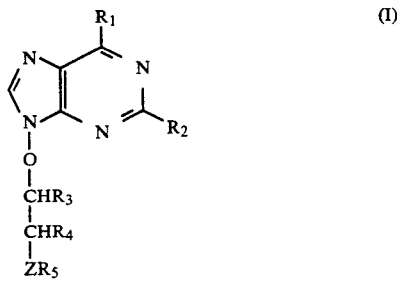

wherein
$R_1$ is hydroxy or amino;
$R_2$ is hydrogen or amino;
$R_3$ is hydrogen, hydroxymethyl or acyloxymethyl;
$R_4$ is hydrogen or (when $R_3 = H$ and Z is a bond or $CH_2$) hydroxy, acyloxy, hydroxymethyl or acyloxymethyl;
Z is a bond, or a group $CHR_8$ wherein $R_8$ is hydrogen, or (when $R_3 = R_4 = H$), $R_8$ is hydroxy, acyloxy, hydroxymethyl or acyloxymethyl;
$R_5$ is a group of formula:

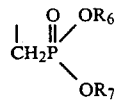

wherein
$R_6$ and $R_7$ are independently selected from hydrogen, $C_{1-6}$ alkyl and optionally substituted phenyl.

When $R_1$ is hydroxy and $R_2$ is amino, the compound of formula (I) is a guanine derivative;
When $R_1$ is amino and $R_2$ is hydrogen, the compound of formula (I) is an adenine derivative;
When $R_1$ is hydroxy and $R_2$ is hydrogen, the compound of formula (I) is a hypoxanthine derivative; and
When $R_1$ and $R_2$ are both amino groups, the compound of formula (I) is a 2,6-diaminopurine derivative.

Often, the compound of formula (I) is a guanine or adenine derivative.

Suitable examples of the acyl groups in $R_3$, $R_4$ and $R_8$ include carboxylic acyl, such as $C_{1-7}$ alkanoyl and benzoyl optionally substituted in the phenyl ring as defined below for $R_6/R_7$. Preferred acyl groups include acetyl, propionyl, butyryl, heptanoyl and hexanoyl.

Suitable examples of $R_6$ and $R_7$ include hydrogen, methyl, ethyl, n- and iso-propyl, n-, sec-, iso- and tert-butyl, and phenyl optionally substituted by one, two or three groups or atoms selected from halogen, such as fluoro, chloro, bromo, and $C_{1-4}$ alkyl or $C_{1-4}$ alkoxy wherein the alkyl moiety is selected from those listed for $R_6/R_7$ above.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

As the compound of formula (I) contains a phosphonate group, suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine.

It will be appreciated that some of the compounds of formula (I), especially those wherein $R_3/R_4/R_8$ is other than hydrogen, have an asymmetric center, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

The compounds of formula (I) including their alkali metal salts may form solvates such as hydrates and these are included wherever a compound of formula (I) or a salt thereof is herein referred to.

It will be appreciated that, when $R_1$ is hydroxy in formula (I) the compound exists in the predominant tautomeric form of structure (IA):

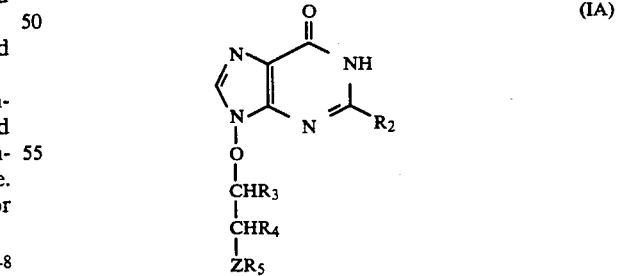

The invention also provides a process for the preparation of a compound of formula (I), or a pharmaceutically acceptable salt thereof, which process comprises either i) imidazole ring closure of a compound of formula (II):

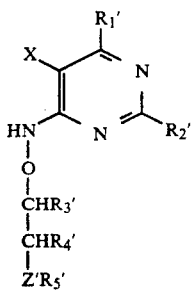

(II)

wherein X is a group capable of cyclising to form an imidazole ring, such as amino or an amino derivative, for example, formylamino; or ii) pyrimidine ring closure of a compound of formula (III):

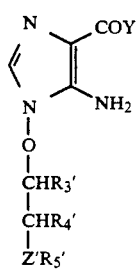

(III)

wherein Y is amino or $C_{1-6}$ alkoxy, with a condensing agent capable of cyclising to form a pyrimidine ring having a 2-$R_2'$ substituent, to give a compound of formula (I) wherein $R_1$ is hydroxy and $R_2$ is amino; or iii) condensing a compound of formula (IV):

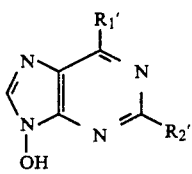

(IV)

with a side chain intermediate of formula (V):

QCHR$_3'$CHR$_4'$Z'R$_5'$     (V)

wherein Q is a leaving group;

and wherein, in formulae (II) to (V), $R_1'$, $R_2'$, $R_3'$, $R_4'$, $R_5'$ are $R_1$, $R_2$, $R_3$, $R_4$ and $R_5$ respectively, or groups or atoms convertible thereto; Z' is Z or Z wherein $R_8$ is $R_8'$ which is a group convertible to $R_8$; and thereafter, when desired or necessary, converting $R_1'$, $R_2'$, $R_3'$, $R_4'$ and/or $R_5'$, when other than $R_1$, $R_2$, $R_3$, $R_4$ and/or $R_5$ to $R_1$, $R_2$, $R_3$, $R_4$ and/or $R_5$ respectively, and/or converting $R_1'$, $R_2'$, $R_3'$, $R_4'$ and/or $R_5'$ when $R_1$, $R_2$, $R_3$, $R_4$ and/or $R_5$, to other $R_1$, $R_2$, $R_3$, $R_4$ and/or $R_5$.

Process i) may be carried out, preferably when X is formyl, using a cyclisation condensing agent, such as diethoxymethyl acetate or triethyl orthoformate, or by fusion.

Process ii) is preferably carried out in accordance with conventional methods.

Process iii) may be carried out with suitable values for Q including halo, such as chloro, bromo and iodo, preferably iodo; or other groups readily displaceable by nucleophiles, such as mesyloxy or tosyloxy. The reaction preferably takes place in an inert solvent, such as dimethylformamide in the presence of a base, such as potassium carbonate, at 0°–50° C., preferably ambient temperature. Alternatively, Q may be OH, in which case the reaction takes place in the presence of a dehydrating catalyst, such as diethylazodicarboxylate in the presence of triphenylphosphine.

Examples of conversions of variable groups are as follows:

$R_1'$–$R_1$ a) An $R_1$ hydroxy group may be converted to $R_1'$ is chloro, by chlorination using a reagent such as phosphorus oxychloride, preferably in the presence of tetraethylammonium chloride and dimethylaniline (as acid acceptor) in $CH_3CN$ at reflux temperatures, according to the method described by M. J. Robins and B. Ozanski Can. J. Chem, 59, 2601 (1981).

b) An $R_1'$ chloro group may be converted to $R_1$ is hydroxy by hydrolysis using aqueous mineral acid, such as hydrochloric acid, or more preferably, using an organic acid, such as formic acid at elevated temperature, suitably 70°–150° C., preferably around 100° C.

c) An $R_1'$ chloro group may be converted to $R_1$ is amino by treatment with ammonia in a lower alkanol, such as ethanol or methanol in an autoclave at 100° C. for a period of about 7 hours, or alternatively, by treatment with sodium azide in dimethylformamide (forming an $R_1$ is $N_3$ intermediate), followed by reduction with ammonium formate/palladium on charcoal, in methanol.

d) An $R_1'$ alkoxy group, such as methoxy, may be converted to $R_1$ hydroxy by the methods of D. R. Haines, J. Med. Chem. 1987, 30, 943 and K. K. Ogilvie and H. R. Hanna, Can. J. Chem. 1984, 62, 2702.

e) An $R_1'$ protected amino group, such as tritylamino, may be converted to amino, by treatment with aqueous acetic acid, preferably 80% acetic acid at elevated temperature, around 80° C. $R_1'$ may also be phthalimido, which may be converted to amino by treatment with methyl hydrazine or hydrazine in an inert solvent, such as dichloromethane, at ambient temperature.

$R_2'$–$R_2$ a) $R_2'$ may be protected amino, such as formylamino, which may be converted to $R_2$ is amino by hydrolysis; or $R_2'$ may be di-tbutyloxycarbonylamino.

$R_3'$–$R_3$, $R_4'$–$R_4$, $R_8'$–$R_8$ a) Hydroxy or hydroxymethyl may be converted to acyloxy or acyloxymethyl respectively by conventional acylation procedures.

b) Protected hydroxy or protected hydroxymethyl may be converted to hydroxy or hydroxymethyl by conventional deprotection methods.

Suitable examples of protecting groups and their removal, are as described in EP-A-242482. A particularly suitable protecting group is the t-butyl-dimethylsilyl group removable by 80% acetic acid at elevated temperature, around 90° C.

$R_5'$–$R_5$

When $R_6$ and $R_7$ in $R_5$ are other than hydrogen, they may be converted to $R_6$ and $R_7$ are hydrogen, using a deesterifying reagent, such as trimethylsilyl bromide in an aprotic solvent such as dichloromethane or dimethylformamide at ambient temperature, as described by C. E. McKenna et. al. J.C.S. Chem. Comm., 1979, 739.

Selective conversion of one of $R_6$ and $R_7$ to hydrogen, may be achieved by treatment with hydroxide ion, as described by Rabinowitz JACS 1960, 82, 4564.

It will be appreciated that the above conversions may take place in any desired or necessary order, having regard to the final desired compound of formula (I). Intermediates of formula (II) may be prepared from a corresponding compound of formula (VI):

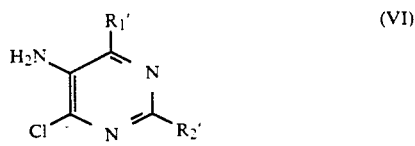

and via intermediates of formula (V) wherein Q is OH, as hereinbefore defined, according to the methods described in EP-A-242482 i.e. by converting the compound of formula (V) wherein Q is OH to the phthalimidooxy derivative followed by reaction with methylhydrazine, as described in the Descriptions hereinafter.

The compound of formula (VI) wherein $R_1'$ is chloro and $R_2'$ is amino, is a known compound as described by Temple et. al. J. Org. Chem., 40 (21), 3141, 1975.

The compound of formula (VI) wherein $R_1'$ is chloro and $R_2'$ is hydrogen is a commercially available compound.

Intermediates of formula (III) may be prepared according to the methods described in EP-A-242482.

Compounds of the formula (IV) are prepared from compounds of formula (VI) wherein the 5-amino group is formylated, by reaction with $R_9ONH_2$ wherein $R_9$ is a protecting group, to give a compound of formula (VII):

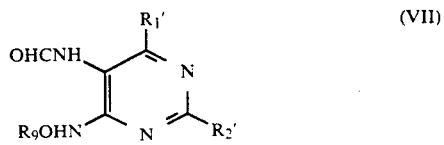

which may be cyclised with diethoxymethyl acetate, to give a compound of formula (IV) wherein the OH group is protected. Suitable values for $R_9$ include benzyl, removable by hydrogenation, and the tetrahydropyran-2-yl group removable by treatment with 80% acetic acid, at ambient temperature.

Intermediates of the formula (V) wherein Q is hydroxy are known compounds or are prepared by analogous methods to those used for structurally similar known compounds.

It will be appreciated that, when $R_3$, $R_4$ and/or $R_8$ is other than hydrogen in the resulting compound of formula (I), synthesis of the intermediate of formula (V) wherein Q is hydroxy may involve selective deprotection of an intermediate wherein Q is protected hydroxy and a hydroxy group in $R_3/R_4/R_8$ is protected.

Intermediates of formulae (II), (III) and (V) but wherein Q is replaced by an aminooxy group, and wherein $R_5'$ is $R_5$ as defined in formula (I), are generally believed to be novel and form an aspect of the invention; other than the compound wherein $R_3'$ and $R_4'$ are both hydrogen, Z' is $CH_2$ and $R_6$ and $R_7$ in $R_5$ are both n-pentyl, disclosed in Izv. Akad. Nauk. SSSR, Ser. Khim., 1092, 1986.

Pharmaceutically acceptable salts may be prepared in conventional manner, for example, in the case of acid addition salts, by reaction with the appropriate organic or inorganic acid.

It will be appreciated that the invention provides a process for the preparation of a compound of formula (I) wherein there is an hydroxy group in $R_3/R_4/R_8$ which process comprises the deprotection of a corresponding compound of formula (I) wherein an hydroxy group in $R_3/R_4/R_8$ is in protected form. Preferred methods for deprotection, as hereinbefore described include removal of the ʹbutyldimethylsilyl group.

The invention also provides a process for the preparation of a compound of formula (I) wherein $R_6$ and $R_7$ are both hydrogen, which process comprises the deesterification of a corresponding compound of formula (I) wherein $R_6$ and $R_7$ are the same alkyl or optionally substituted phenyl group.

The compounds of the invention are of potential use in the treatment of infections caused by viruses, especially herpesviruses such as herpes simplex type 1, herpes simplex type 2; varicella-zoster virus, Epstein-Barr virus and cytomegalovirus; and lentiviruses such as visna virus and human immunodeficiency virus.

The compounds may also be inhibitors of tumorogenic viruses and/or of potential use in the treatment of neoplastic diseases, i.e. cancer.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No unacceptable toxicological effects are indicated at the above described dosage levels.

The invention also provides a method of treating viral infections in a human or non-human animal, which comprises administering to the animal an effective, non-toxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The compounds of the invention are also believed to exhibit a synergistic antiviral effect in conjunction with interferons; and combination products comprising these two components for sequential or concomitant administration, by the same or different routes, are therefore within the ambit of the present invention.

The following examples illustrate the invention; the following descriptions illustrate the preparation of intermediates.

DESCRIPTION 1

(Intermediates for Examples 1,2,9 and 10)

a) Diethyl 3-(N-phthalimidooxy)propylphosphonate

A mixture of N-(3-bromopropoxy)phthalimide (20.79 g, 73.2 mmol) and triethyl phosphite (12.81 ml, 74 mmol) was heated at 150° C. for 4 hours. The solution was cooled to ambient temperature and chromatographed on silica gel (eluting initially with hexane: ethyl acetate (40:60), then ethyl acetate) to yield the title compound as a colorless oil (18.12 g, 72%). $^1$H NMR: $\delta$H (CDCl$_3$) 1.34 (6H, t, J=7.1Hz, (OC$\underline{H}_2$CH$_3$)$_2$), 2.0–2.25(4H, m, C$\underline{H}_2$CH$_2$P), 4.05–4.2 (4H, m, (OC$\underline{H}_2$CH$_3$)$_2$), 4.27 (2H, t, J=5.7Hz, —OC$\underline{H}_2$), 7.8 (4H, m, aromatic H). m/z: C$_{15}$H$_{21}$NO$_6$P requires: 342.1107. Observed: 342.1101(MH$^+$).

b) Diethyl 3-(aminooxy)propylphosphonate

Methylhydrazine (0.44 ml, 8.35 mmol) was added dropwise to a solution of diethyl 3-(N-phthalimidooxy)-propyl-phosphonate (1.9 g, 5.6 mmol) in dichloromethane (15 ml) at 0° C. The reaction mixture was stirred for 1 hour and left at ambient temperature overnight. The solution was filtered, the filtrate evaporated and the oily residue chromatographed on silica gel (eluting with ethyl acetate, then ethyl acetate-ethanol (20:1)) to yield the title compound as a colorless oil (0.8 g, 68%). $^1$H NMR: $\delta$H (CDCl$_3$) 1.32 (6H, t, J=7.1Hz, (OC$\underline{H}_2$CH$_3$)$_2$), 1.72–2.05 (4H, m, C$\underline{H}_2$CH$_2$P), 3.70 (2H, t, J=6Hz, NOC$\underline{H}_2$), 4.0–4.2 (4H, m, (OC$\underline{H}_2$CH$_3$)$_2$), 4.75 (2H, broad, D$_2$O exchangeable NH$_2$). m/z: C$_7$H$_{18}$NO$_4$P requires 211.0973. Observed: 211.0975 (M$^+$).

DESCRIPTION 2

(Intermediates for Examples 1 and 2)

a) 4-Chloro-6-[[3-(diethoxyphosphoryl)propoxy]amino]-2,5-diformamidopyrimidine

A mixture of 4,6-dichloro-2,5-diformamidopyrimidine (1.48 g, 6.3 mmol), diethyl 3-(aminooxy)propyl-phosphonate (1.33 g, 6.3 mmol), diisopropylethylamine (2.19 ml, 12.6 mmol) in diglyme (20 ml) was heated at 100° C. for 1½ hours. After cooling, the solvent was removed under reduced pressure. The residue was chromatographed on silica gel (dichloromethane-methanol (97:3) as eluant) to give the title compound as a yellow foam (1.15 g, 58% based on recovered pyrimidine). $^1$H NMR: $\delta$H ((CD$_3$)$_2$SO+D$_2$O) 1.21 (6H, t, J=7H$_z$, (OCH$_2$C$\underline{H}_3$)$_2$), 1.65–2.00 (4H, m, C$\underline{H}_2$CH$_2$P), 3.85–4.05 (6H, m, N—OC$\underline{H}_2$, (OC$\underline{H}_2$CH$_3$)$_2$), 7.90+8.15 (1H, 5-NHCHO), 9.25 (2-NHCHO) Found: C, 38.12; H, 5.15; N, 16.25%. C$_{13}$H$_{21}$N$_5$O$_6$P$\overline{C}$l requires: C, 38.10; H, 5.17; N, 17.09%.

b) 6-Chloro-9-[3-(diethoxyphosphoryl)propoxy]-2-formamidopurine

A solution of 4-chloro-6-[[3-(diethoxyphosphoryl)-propoxy]amino]-2,5-diformamidopyrimidine (1.1 g, 2.7 mmol) in diethoxymethyl acetate (15 ml) was heated at 120° C. for 2 hours. The solution was then cooled, evaporated to dryness under reduced pressure and the residue obtained dissolved in methanol (10 ml) and 880 ammonia (1 ml). After standing at ambient temperature for 1 hr, the solvent was removed. The residue was chromatographed on silica gel (dichloromethane-methanol (98:2) as eluant) to give the title compound as a colorless oil which crystallised on standing, mp. 121°–124°, (1.01 g, 95%). IR: $\nu$max (KBr) 1700, 1618, 1577, 1506, 1439, 1405, 1383, 1328, 1259, 1242, 1226, 1165, 1052, 1024, 972, 918 cm$^{-1}$. $^1$H NMR: $\delta$H ((CD$_3$)$_2$SO) 1.21 (6H, t, J=7Hz, (O—CH$_2$C$\underline{H}_3$)$_2$), 1.75–2.1 (4H, m, C$\underline{H}_2$CH$_2$P), 3.99 (4H, m, (OC$\underline{H}_2$CH$_3$)$_2$), 4.47 (2H, t, J=6Hz, N—OC$\underline{H}_2$), 8.83 (1Y, s, H—8), 9.37 (1H, s, C$\underline{H}$O), 11.30 (1H, bs, D$_2$O exchangeable, N$\underline{H}$CHO). Found: C, 39.82; H, 4.96; N, 17.65%. C$_{13}$H$_{19}$N$_5$O$_5$ClP requires: C, 39.85; H, 4.89; N, 17.88%. m/z: C$_{13}$H$_{20}$N$_5$O$_5$PCl requires: 392.0890. Observed: 392.0888 (MH$^+$).

DESCRIPTION 3

(Intermediates for Examples 3–8)

a) Diethyl 4-hydroxybutylphosphonate

Diethyl 4-(tert-butyldimethylsilyloxy)butylphosphonate (1.7 g, 5.25 mmol) was dissolved in 80% acetic acid (5 ml) and the resulting solution was stirred at 70° C. for 20 min. The reaction mixture was then allowed to cool and water (2 ml) was added. The resulting mixture was washed with hexane (3×5 ml) and chloroform (5×5 ml). The combined chloroform phase was washed with sat. aq. NaHCO$_3$ (2×10 ml), water (1×10 ml) and the solvents were evaporated under vacuum. The residue was chromatographed on silica gel (eluted with chloroform: ethanol 96:4) to give the title compound as a colorless oil (1 g, 91%). $^1$H NMR:$\delta$H ((CD$_3$)$_2$SO), 1.22 (6H, t, J=7Hz, (OCH$_2$C$\underline{H}_3$)$_2$), 1.47 (4H, br.s, C$\underline{H}_2$CH$_2$), 1.68 (2H, m, C$\underline{H}_2$P), 3.38 (2H, br.s, HOC$\underline{H}_2$), 3.96 (4H, m, (OC$\underline{H}_2$CH$_3$)$_2$), 4.43 (1H, br.s, HOC$\underline{H}_2$, D$_2$O exchangeable).

b) Diethyl 4-(N-phthalimidooxy)butylphosphonate

To a cooled solution of diethyl 4-hydroxybutylphosphonate (4.41 g, 21 mmol), diethyl azodicarboxylate (4.02 g, 23.1 mmol, 1.1 meq) and N-hydroxyphthalimide (3.42 g, 21 mmol) in THF (50 ml), triphenylphosphine (6.05 g, 23.1 mmol, 1.1 meq) in THF (30 ml) was added drop-wise over 1 hour. The reaction mixture was stirred at 23° C. for 16 hr. The solvent was evaporated, the residue was dissolved in diethyl ether and the resulting solution was stirred at 0° C. for 3 hr. Triphenyl phosphine oxide was filtered off and washed with diethyl ether. The combined diethyl ether solutions were evaporated to dryness and the residue was purified by column chromatography on silica gel (eluted with acetone: petroleum ether (60°–80° C.) (30:70)) to give the title compound (5.82 g, 78%). $^1$H NMR:$\delta$H ((CD$_3$)$_2$SO) 1.23 (6H, t, J=7Hz (OCH$_2$C$\underline{H}_3$)$_2$), 1.74 (6H, m, C$\underline{H}_2$CH$_2$CH$_2$P), 4.14(2H,t,OC$\underline{H}_2$), 3.98 (4H, m, (OC$\underline{H}_2$CH$_3$)$_2$) 7.86 (4H, s, phthalyl H).

c) Diethyl 4-(aminooxy)butylphosphonate

To a solution of diethyl 4-(N-phthalimidooxy)butylphosphonate (2.1 g 5.9 mmol) in dry dichloromethane (25 ml) was added methylhydrazine (0.313 ml, 5.9 mmol). The reaction mixture was stirred at 23° C. for 6 hr; the precipitate was then filtered off, washed with dichloromethane and the solution concentrated to an oil. The residue was purified by column chromatography on silica gel (eluted with chloroform-ethanol, 98:2) to give the title compound as a colorless oil (1 g, 75%). $^1$H NMR: $\delta$H ((CD$_3$)$_2$SO) 1.22 (6H, t, J=7Hz, (OCH$_2$CH$_3$)$_2$), 1.51 (4H, m, CH$_2$CH$_2$), 1.70 (2H, m, CH$_2$P), 3.5 (2H, t, J=6Hz, OCH$_2$), 3.96 (4H, m, (OCH$_2$CH$_3$)$_2$), 5.87 (2H, br.s, D$_2$O exchangeable, NH$_2$).

DESCRIPTION 4

(Intermediates for Examples 3-6)

a) 4-Chloro-6-[[4-(diethoxyphosphoryl)butoxy]amino]-2,5-diformamidopyrimidine 4,6-Dichloro-2,5-diformamidopyrimidine (0.35 g, 1.5 mmol), diethyl 4-(aminooxy)butylphosphonate (0.216 g, 0.93 mmol) and N,N-diisopropylethylamine (0.521 ml, 3 mmol) were dissolved in diglyme (15 ml) and stirred at 100° C. for 3 hr. The reaction mixture was then allowed to cool, the hydrochloride of N,N-diisopropylethylamine was filtered off and the filtrate was diluted with chloroform (150 ml). The resulting solution was washed with 4% aq. NaHCO$_3$ (1×20 ml) and water (1×20 ml). The combined aqueous layers were extracted with chloroform (4×20 ml) and the combined chloroform solutions were evaporated to dryness. The residue was chromatographed on silica gel (eluted with chloroform-ethanol, 96:4) to yield the title compound (0.330 g, 81%). $^1$H NMR: $\delta$H ((CD$_3$)$_2$SO) 1.22 (6H, t, J=7Hz, (OCH$_2$CH$_3$)$_2$), 1.7 (6H, m, CH$_2$CH$_2$CH$_2$P), 3.87 (2H, t, J=5Hz, OCH$_2$), 3.98 (4H, m, (OCH$_2$CH$_3$)$_2$) 8.14 (1H, s, 5-NHCHO), 8.31 (1H, s, 6-NHCHO), 9.24 (1H, br.s, 2-NHCHO), 9.41 (1H, br.s, D$_2$O exchangeable, NHOCH$_2$), 10.81 (2H, br.s, D$_2$O exchangeable, NHCHO, NHCHO).

b) 6-Chloro-9-[4-(diethoxyphosphoryl)butoxy]-2-formamidopurine

4-Chloro-6-[[4-(diethoxyphosphoryl)butoxy]amino]-2,5-diformamidopyrimidine (0.330 g, 0.78 mmol) was dissolved in diethoxymethyl acetate (4 ml) and the resulting solution was stirred at 120° C. for 2 hr. The reaction mixture was then allowed to cool and evaporated to dryness. The residue was dissolved in methanol: conc. aq. NH$_3$ solution (9:1, 5 ml) and stirred at 23° C. for 5 min. The solvents were evaporated under vacuum and the product was purified by column chromatography on silica gel (eluted with chloroform: ethanol, 96:4) to yield the title compound (0.225 g, 71%), m.p. 98° C. (acetonitrile). $^1$H NMR: $\delta$H ((CD$_3$)$_2$SO) 1.22 (6H, t, J=7Hz, (OCH$_2$CH$_3$)$_2$), 1.76 (6H, m, CH$_2$CH$_2$CH$_2$P), 3.98 (4H, m, (OCH$_2$CH$_3$)$_2$), 4.43 (2H, t, J=6Hz, NOCH$_2$), 8.8 (1H, s, H-8) 9.36 (1H, br.s, NHCHO), 11.29 (1H, br.s, D$_2$O exchangeable, NHCHO).

DESCRIPTION 5

(Intermediates for Examples 7 and 8)

a) 4-Chloro-6-[[4-(diethoxyphosphoryl)butoxy]amino]-5-formamidopyrimidine 4,6-Dichloro-5-formamidopyrimidine (0.441 g, 2.3 mmol), diethyl 4-(aminooxy)butylphosphonate (0.4 g, 1.77 mmol) and N,N-diisopropylethylamine (0.8 ml, 4.6 mmol) in diglyme (15 ml) were stirred at 100° C. for 2.5 hr. The reaction mixture was then allowed to cool, the hydrochloride of N,N-diisopropylethylamine was filtered off and the filtrate was diluted with chloroform (150 ml). The resulting solution was washed with 4% aq. NaHCO$_3$ (1×20 ml) and water (1×20 ml). The combined aqueous layers were extracted with chloroform (6×20 ml) and the combined chloroform solutions were concentrated to an oil. The residue was chromatographed on silica gel (eluted with chloroform: ethanol, 96:4) to yield the title compound (0.520 g, 77%). $^1$H NMR: $\delta$H [(CD$_3$)$_2$SO] 1.22 (6H, t, J=7Hz, (OCH$_2$CH$_3$)$_2$), 1.68 (6H, m, CH$_2$CH$_2$CH$_2$P), 3.9 (2H, m, NOCH$_2$), 3.97 (4H, m, (OCH$_2$CH$_3$)$_2$), 8.14 (1H, s, H-2), 9.5 (1H, br.s, NHOCH$_2$, D$_2$O exchangeable), 11.0 (1H, NHCHO, D$_2$O exchangeable).

b) 6-Chloro-9-[4-(diethoxyphosphoryl)butoxy]purine

4-Chloro-6-[[4-(diethoxyphosphoryl)butoxy]amino]-5-formamidopyrimidine (0.470 g, 1.24 mmol) was dissolved in diethoxymethyl acetate (4 ml) and the resulting solution was stirred at 120° C. for 2 hr. The reaction mixture was then allowed to cool and the solution evaporated to dryness. The residue was dissolved in methanol: conc. aq. NH$_3$ solution (9:1, 5 ml) and stirred at 23° C. for 10 min. The solvents were evaporated under vacuum and the product was purified by column chromatography on silica gel (eluted with chloroform: ethanol, 98:2) to yield the title compound (0.360 g, 81%). $^1$H NMR: $\delta$H [(CD$_3$)$_2$SO] 1.34 (6H, t, J=7Hz, (OCH$_2$CH$_3$)$_2$), 1.89 (6H, m, CH$_2$CH$_2$CH$_2$P), 4.12 (4H, m, (OCH$_2$CH$_3$)$_2$), 4.51 (2H, t, J=6Hz, NOCH$_2$), 8.28 (1H, s), 8.78 (1H, s). m/z (FAB positive ion) 363 (MH$^+$).

DESCRIPTION 6

(Intermediates for Examples 9 and 10)

a) 4-Chloro-6-[[3-(diethoxyphosphoryl)propoxy]amino]-5-formamidopyrimidine

A mixture of 4,6-dichloro-5-formamidopyrimidine (2.82 g, 14.6 mmol), diethyl 3-(aminooxy)propylphosphonate (3.1 g, 14.6 mmol) and triethylamine (3.1 ml, 22.3 mmol) in dioxan (40 ml) was heated at 100° C. for 4 hours. The solution was cooled to ambient temperature, filtered, and the filtrate evaporated to give a yellow oil. The oil was purified by column chromatography on silica gel (eluting with chloroform: methanol 97:3) to give the title compound as a yellow oil (4.4 g, 74%). $^1$H NMR: $\delta$H (CDCl$_3$) 1.3 (6H, t, J=7Hz, (OCH$_2$CH$_3$)$_2$), 1.6-2.5 (4H, m, CH$_2$CH$_2$P), 3.9-4.5 (6H, m, N—OCH$_2$, (OCH$_2$CH$_3$)$_2$), 7.3-9.3 (3H, broad, —NH CHO, —NH—OCH$_2$).

b) 6-Chloro-9-[3-(diethoxyphosphoryl)propoxy]purine

A solution of 4-chloro-6-[[3-(diethoxyphosphoryl)propoxy]amino]-5-formamidopyrimidine (0.86 g, 2.3 mmol) in diethoxymethyl acetate (5 ml) was heated at 120° C. for 2 hours. After cooling to ambient temperature, excess solvent was removed under reduced pressure to leave an oil. The oil was dissolved in methanol (20 ml) and 880 ammonia (0.5 ml) was added. After 20 minutes at ambient temperature, the solvent was evaporated to leave an oil. Purification by column chromatography on silica gel (dichloromethane:methanol, 96:4 as eluant) gave the title compound as a yellow oil (0.7 g, 85%). IR: $\nu$max 3065, 3000, 1595, 1560, 1330, 1240, 1215, 1160, 1050, 1025, 960 and 930 cm$^{-1}$. $^1$H NMR: $\delta$H [(CD$_3$)$_2$SO] 1.22 (6H, t, J=7Hz, (OCH$_2$CH$_3$)$_2$), 1.6-2.1

(4H, m, OCH$_2$CH$_2$CH$_2$P), 4.00 (4H, m, (OCH$_2$CH$_3$)$_2$), 4.50 (2H, t, J=6Hz, OCH$_2$), 8.8 (1H, s), 9.05 (1H, s).

DESCRIPTION 7

(Intermediates for Examples 11 and 12)

a) Diethyl but-3-enylphosphonate

Diethyl phosphite (4.14 g, 0.03 mol) was added to a suspension of 60% sodium hydride (1.2 g, 0.03 mol) in dry tetrahydrofuran (60 ml) at ambient temperature. The mixture was stirred for 5 minutes until a pale yellow solution was obtained. 4-Bromobut-1-ene (4.5 g, 0.033 mol) was added dropwise and the reaction mixture heated at reflux for 3 hours. After cooling to ambient temperature and filtering, the filtrate was concentrated under reduced pressure to give an oil. The oil was chromatographed on silica gel (eluting with ethyl acetate-hexane, 50:50) to yield the title compound as a colorless oil (3.85 g, 67%). IR: υmax (film) 3080, 3000, 2940, 2920, 2880, 1645, 1450, 1390, 1260, 1165, 1060, 1030, 970, 820, 790 cm$^{-1}$. $^1$H NMR: δH (CDCl$_3$) 1.35 (6H, t, J=7Hz, (OCH$_2$CH$_3$)$_2$), 1.50-2.70 (4H, m, CH$_2$CH$_2$P), 4.10 (4H, m, (OCH$_2$CH$_3$)$_2$) 4.85-5.28 (2H, m, CH$_2$=CH), 5.5-6.28 (1H, m, CH$_2$=CH—CH$_2$).

b) Diethyl 3,4-dihydroxybutylphosphonate

To a solution of diethyl but-3-enylphosphonate (10.2 g, 0.053 mol) in acetone (200 ml) and water (40 ml), was added a trace of osmium tetroxide (1 mg). After stirring for 10 minutes at ambient temperature, 4-methylmorpholine-N-oxide (10.75 g, 0.079 mol) was added in one portion. Stirring was continued overnight under an atmosphere of nitrogen. The solution was concentrated under reduced pressure, and final traces of water removed by azeotroping with benzene and ethanol. The residual brown oil was chromatographed on silica gel (dichloromethane-methanol, 95:5 as eluant) to give the title compound as an oil (8.5 g, 71%). IR: υmax (film), 3400, 3000, 2940, 2880, 1450, 1400, 1230, 1170, 1070, 1030, 970, 820, 790 cm$^{-1}$. $^1$H NMR: δH ((CD$_3$)$_2$SO) 1.25 (6H, t, J=8Hz, (OCH$_2$CH$_3$)$_2$), 1.3-2.05 (4H, m, CH$_2$CH$_2$P), 3.1-3.5 (3H, m, HOCH$_2$CH(OH)), 4.0 (4H, m, (OCH$_2$CH$_3$)$_2$), 4.6 (2H, m, D$_2$O exchangeable, HOCH$_2$CH(OH)). Found: C, 42.57; H, 8.56%. C$_8$H$_{19}$O$_5$P requires: C, 42.47; H, 8.46%. m/z:C$_8$H$_{20}$O$_5$P requires 227.1048; observed: 227.1045 (MH+).

c) Diethyl [4-(t-butyldimethylsilyloxy)-3-hydroxybutyl]phosphonate

To a solution of diethyl 3,4-dihydroxybutylphosphonate (8.5 g, 0.038 mol) in dry tetrahydrofuran (200 ml) was added imidazole (5.25 g, 0.077 mol). After stirring at ambient temperature for 2 minutes, t-butyldimethysilyl-chloride (5.8 g, 0.038 mol) was added. After 18 hours, the solution was filtered and the filtrate evaporated to give a colorless oil. The oil was dissolved in ether, and washed with water. The organic phase was dried (magnesium sulphate) and evaporated to give an oil which was purified by chromatography on silica gel (dichloromethane-methanol (98:2) as eluant). The title compound was obtained as an oil (8 g, 62%). IR:υmax (film), 3400, 2940, 2860, 1250, 1170, 960, 840, 780 cm$^{-1}$. $^1$H NMR: δH (CDCl$_3$) 0.00 (6H, s, SiMe$_2$), 0.83 (9H, s, SiBu$^t$), 1.25 (6H, t, J=7Hz, (OCH$_2$CH$_3$)$_2$), 1.5-2.0 (4H, m, CH$_2$CH$_2$P), 2.7 (1H, bs, D$_2$O exchangeable, OH), 3.35-3.65 (3H, m, OCH$_2$CH), 4.0 (4H, m, (OCH$_2$CH$_3$)$_2$) Found: C, 48.66; H, 9.83%. C$_{14}$H$_{33}$O$_5$SiP requires: C, 49.39; H, 9.77%.

d) Diethyl [4-(t-butyldimethylsilyloxy)-3-(phthalimidooxy)butyl]phosphonate

Diethyl azodicarboxylate (4.02 ml, 0.0.26 mol) was added to a solution of diethyl [4-(t-butyldimethylsilyloxy)-3-hydroxybutyl]phosphonate (7.9 g, 0.023 mol), N-hydroxyphthalimide (3.79 g, 0.023 mol) and triphenylphosphine (6.70 g, 0.026 mol) in dry tetrahydrofuran (100 ml). The mixture was stirred overnight at ambient temperature under a nitrogen atmosphere. The solvent was removed in vacuo and the residue dissolved in diethyl ether and kept at 4° C. for 24 hours. The mixture was filtered and the filtrate evaporated to dryness. The residue was chromatographed on silica gel (hexane-acetone 3:1 as eluant) to give the title compound as a pale yellow oil (7.9 g, 70%). IR:υmax (film) 2990, 2960, 2940, 2860, 1790, 1740, 1605, 1420, 1370, 1250, 1190, 1160, 1120, 1060, 1030, 970, 880, 840, 790, 700 cm$^{-1}$. $^1$H NMR: δH (CDCl$_3$) 0.0 (6H, s, SiMe$_2$), 0.8 (9H, s, SiBu$^t$), 1.3 (6H, t, J=7Hz, (OCH$_2$CH$_3$)$_2$), 1.78-2.4 (4H, m, CH$_2$CH$_2$P), 3.6-4.1 (7H, m, OCH$_2$CH +(OCH$_2$CH$_3$)$_2$), 7.65-7.95 (4H, m, aromatic H).

e) Diethyl [4-(t-butyldimethylsilyloxy)-3-(aminooxy)-butyl]phosphonate

Methylhydrazine (0.97 ml, 18 mmol) was added to a solution of diethyl [4-(t-butyldimethylsilyloxy)-3-(phthalimidooxy)butyl]phosphonate (5.9 g, 12 mmol) in dichloromethane (40 ml). A white solid separated after a few minutes. The mixture was stirred overnight, filtered, the solvent evaporated and the residue chromatographed on silica gel using dichloromethane-methanol (98:2) as eluant. The title compound was obtained as a colorless oil (3.05 g, 70%). IR: υmax (film). 3320, 2970, 2940, 2860, 1595, 1470, 1390, 1250, 1160, 1060, 1030, 960, 840, 780, cm$^{-1}$. $^1$H NMR: δH (CDCl$_3$) 0.08 (6H, s, SiMe$_2$), 0.9 (9H, s, SiBu$^t$), 1.3 (6H, t, J=7Hz, (OCH$_2$CH$_3$)$_2$), 1.5-2.2 (4-H, m, CH$_2$CH$_2$P), 3.4-3.9 (3H, m, OCH$_2$CH), 4.15 (4H, m, (OCH$_2$CH$_3$)$_2$), 5.3 (2H, broad, D$_2$O exchangeable NH$_2$).

f) 6-[[1-(t-Butyldimethylsilyloxymethyl)-3-(diethoxyphosphoryl)propoxy]amino]-4-chloro-5-formamidopyrimidine A mixture of 4,6-dichloro-5-formamidopyrimidine (0.73 g, 3.8 mmol), diethyl [4-(t-butyldimethylsilyloxy)-3-(aminooxy)butyl]phosphonate (1.35 g, 3.8 mmol) and triethylamine (0.78 ml, 5.7 mmol) in dioxan (20 ml) was heated at 90° C. for 3 hours. After cooling to ambient temperature, the mixture was filtered and the filtrate evaporated. The residue was chromatographed on silica gel using dichloromethane-methanol (98:2) as eluant to yield the title compound as a oil (0.56 g, 29). IR: υmax (film) 3180, 2940, 2870, 1690, 1635, 1250, 1030, 970, 830, 780 cm$^{-1}$. $^1$H NMR: δH (CDCl$_3$) 0.05 (6H, s, SiMe$_2$), 0.9 (9H, s, SiBu$^t$), 1.3 (6H, t, J=7Hz, (OCH$_2$CH$_3$)$_2$), 1.6-2.3 (4H, m, CH$_2$CH$_2$P), 3.6-4.3 (7H, m, OCH$_2$CH +(OCH$_2$CH$_3$)$_2$), 7.3-10.05 (4H, broad, —NH CHO+—NHO+H-2).

g) 9-[1-(t-Butyldimethylsilyloxymethyl)-3-(diethoxyphosphoryl)propoxy]-6-chloropurine A solution of 6-[[1-(t-butyldimethylsilyloxymethyl)-3-(diethoxyphosphoryl)propoxy]amino]-4-chloro-5-formamidopyrimidine (0.5 g) in diethoxymethyl acetate (5 ml) was heated at 110° C. for 2 hours. The solvent was evaporated under reduced pressure, the residue dissolved in methanol (5 ml) and 0.880 ammonia (0.1 ml) added. After 30 minutes at ambient temperature, the solvent was evaporated and the residue chromatographed on silica gel using dichloromethane-methanol (98:2) as eluant. This afforded the title compound (0.27 g, 56%) as a yellow oil. IR: υmax (film) 2940, 2870, 1595, 1565, 1440, 1390, 1340, 1250, 1220, 1060, 1030, 970, 930, 840, 790 cm$^{-1}$. $^1$H NMR: δH (CDCl$_3$) 0.0 (6H, s, SiMe$_2$), 0.8 (9H, s, SiBu$^t$), 1.25 (6H, t, J=7Hz, (OCH$_2$CH$_3$)$_2$), 1.8-2.4 (4H, m, CH$_2$CH$_2$P) 3.8 (2H, d, J=6Hz, CH$_2$OSi), 4.1 (4H, m, (OCH$_2$CH$_3$)$_2$), 4.6 (1H, m, CHON), 8.35 (1H, s), 8.75 (1H, s). Found: C, 45.97; H, 6.89; N, 10.80%. C$_{19}$H$_{34}$N$_4$O$_5$PSiCl requires: C, 46.28; H, 6.95; N, 11.36%.

h) 9-[1-(t-Butyldimethylsilyloxymethyl)-3-(diethoxyphosphoryl)propoxy]adenine

A solution of 9-[1-(t-butyldimethylsilyloxymethyl)-3-(diethoxyphosphoryl)propoxy]-6-chloropurine (0.30 g) in ethanol (10 ml) saturated with ammonia gas was heated in a sealed vessel at 100° C. for 2 hours. The reaction mixture was cooled to ambient temperature overnight, the ethanol evaporated under reduced pressure and the residue chromatographed on silica gel using dichloro-methane-methanol (98:2) as eluant. Starting material (0.06 g) was recovered and the eluant was changed to dichloromethane-methanol (95:5) to afford the title compound (0.10 g, 43%) as an oil. $^1$H NMR: δH ((CD$_3$)$_2$SO) 0.00, 0.61 (6H, 2 x s, SiMe$_2$). 0.81 (9H, s, SiBu$^t$), 1.20 (6H, t, J=7Hz, (OCH$_2$CH$_3$)$_2$), 1.7-2.2 (4H, m, —CH$_2$CH$_2$P), 3.82 (2H, d, J=4.1 H, CH$_2$OSi), 4.0 (4H, m, (OCH$_2$CH$_3$)$_2$), 4.44 (1H, m, OCHCH$_2$), 7.35 (2H, s, D$_2$O exchangeable, N$_2$), 8.3 (1H, s), 8.27 (1H, s). Found: C, 47.82; H, 7.61; N, 14.41%. C$_{19}$H$_{36}$N$_5$O$_5$SiP requires: C, 48.16; H, 7.66; N, 14.79%. m/z: C$_{19}$H$_{36}$N$_5$O$_5$SiP requires: 473.2221. Observed: 473.2219.

DESCRIPTION 8

(Intermediates for Example 13)

a) 6-Benzyloxyamino-4-chloro-2,5-diformamidopyrimidine

A mixture of 4,6-dichloro-2,5-diformamido-pyrimidine (1.9 g, 8.09 mmol), benzyloxyamine (1 g, 8.13 mmol), triethylamine (2 ml) and dioxan (20 ml) was stirred at 100° C. for 1 hour. The cooled reaction mixture was filtered and the precipitate collected and washed with dioxan (2×5 ml). The filtrate and washings were combined and evaporated to a syrup. Column chromatography on silica gel (eluted with chloroform-ethanol, 30:1) afforded the title compound (1.2 g, 46). IR: υmax (KBr) 3242, 1694, 1588, 1472cm$^{-1}$; $^1$H NMR δH [(CD$_3$)$_2$SO], 4.89 (2H, s, OCH$_2$Ph), 7.4 (5H, m, Ph), 8.15 (1H, s, CHO), 9.18, 9.42 (1H, 2 x br.s, D$_2$O exchangeable, NH), 9.25 (1H, br.s, CHO), 10.91 (2H, br.s, D$_2$O exchangeable, 2 x NH). m/z (FAB +ve ion, thioglycerol) MH+322.

b) 9-Benzyloxy-6-chloro-2-formamidopurine

6-Benzyloxyamino-4-chloro-2-formamidopyrimidine (1.2 g, 3.73 mmol) and diethoxymethyl acetate (20 ml) was stirred at 120° C. for 2.5 hours, cooled and evaporated under reduced pressure. A solution of the residue in methanol (20 ml) and 0.880 ammonia (2 ml) was stirred at 20° C. for 1 hour, the solvent removed under reduced pressure and the residue co-evaporated with methanol. Column chromatography on silica gel (eluted with chloroform-ethanol, 100:1) afforded the title compound (700 mg, 62%). IR: υmax (KBr) 3119, 1702, 1611, 1577, 1505, 1440cm$^{-1}$; $^1$H NMR: δH [(CD$_3$)$_2$SO], 5.44 (2H, s, CH$_2$Ph), 7.45 (5H, m, Ph), 8.54 (1H, s, H-8), 9.34 (1H, s, CHO), 11.30 (1H, br.s, D$_2$O exchangeable, NH). Found: C, 49.99; H, 3.37; N, 22.43%, m/z 303.0523. C$_{13}$H$_{10}$N$_5$O$_2$Cl+0.5 H$_2$O requires: C, 49.92; H, 3.55; N, 22.40%, m/z 303.0520.

c) 2-Amino-9-benzyloxy-6-methoxypurine

A mixture of 9-benzyloxy-6-chloro-2-formamidopurine (440 mg, 1.60 mmol), 1.2M sodium methoxide in methanol (5.3 ml) and methanol (10 ml) was heated at reflux temperature for 1 hour and then cooled. Acetic acid (4 ml) was added and the solution evaporated to dryness. The residue was suspended in water and extracted with chloroform (2×25 ml). The combined chloroform extracts were washed with brine, dried (magnesium sulphate) and evaporated under reduced pressure. Column chromatography on silica gel (eluted with chloroform-methanol, 100:1) afforded the title compound (331 mg, 76%). IR: υ$_{max}$ (KBr) 3480, 3310, 1625, 1585, 1505, 1485, 1460, 1400 cm$^{-1}$; $^1$H NMR: δ$_H$ [(CD$_3$)$_2$SO] 3.96 (3H, s, CH$_3$), 5.31 (2H, s, CH$_2$Ph), 6.64 (2H, br.s, D$_2$O exchangeable, NH$_2$), 7.42 (5H, s, Ph), 7.75 (1H, s, H-8). Found: C, 57.18, H, 4.84; N, 25.85). m/z 271.1075. C$_{13}$H$_{13}$N$_5$O$_2$ requires: C, 57.56, H, 4.83, N, 25.82%; m/z 271.1069.

d) 9-Benzyloxy-2-[(bis-t-butoxycarbonyl)amino]-6-methoxypurine

A solution of 2-amino-9-benzyloxy-6-methoxypurine (0.47 g; 1.73 mmol), di-t-butyldicarbonate (0.57 g; 2.60 mmol) and 4-N,N-dimethylaminopyridine (100 mg, 0.173 mmol) in tetrahydrofuran was heated at reflux for 45 minutes. Additional di-t-butyldicarbonate (0.20 g) was then added and the solution refluxed for 30 minutes. The reaction was then cooled and the solvent removed under reduced pressure. The residue was purified by column chormatography on silica gel eluting with chloroform-methanol mixtures, affording the title compound (740 mg; 91%). IR: υ$_{max}$ (KBr) 3110, 2990, 1760, 1600, 1485, 1460, 1400 cm$^{-1}$; $^1$H NMR: δ$_H$ (CDCl$_3$) 1.50(18H, s, 6 x CH$_3$), 4.15(3H, s, CH$_3$), 5.45(2H, s, CH$_2$), 7.35(5H, s, Ar), 7.65(1H, s, H-8).

e) 2-[(Bis-t-butoxycarbonyl)amino]-9-hydroxy-6-methoxypurine

A mixture of 9-benzyloxy-2-[(bis-t-butoxycarbonyl)-amino]-6-methoxypurine (990 mg; 2.10 mmol), 10% palladium on charcoal (100 mg), ethanol (25 ml) and dioxan (25 ml) was stirred at 20° C. under an atmosphere of hydrogen for 45 minutes. The suspension was then filtered and the filtrate evaporated under reduced pressure. The resulting white solid was dried to yield the title compound (760 mg; 95%). IR: υ$_{max}$(KBr) 2990, 2420, 1750, 1740, 1730, 1710, 1605, 1480 cm$^{-1}$; $^1$H NMR δ$_H$[(CD$_3$)$_2$SO] 1.40(18H, s, 6 x CH$_3$), 4.05(3H, s, OCH$_3$), 8.05(1H, s, H-8), 11.8(1H, br.s, D$_2$O exchangeable, OH). Found: C, 50.27; H, 6.12; N, 17.70%. C$_{16}$H$_{23}$N$_5$O$_6$+0.2 EtOH requires: C, 50.42; H, 6.23; N, 17.66%.

f) Diethyl [3-(tert-butyldimethylsilyloxy)-4-hydroxybutyl)]phosphonate

A solution of diethyl (3,4-dihydroxybutyl)phosphonate (3.6 g, 15.92 mmol), tert-butyldimethylsilyl chloride (5.25 g, 35 mmol) and imidazole (5.5 g, 77 mmol) in dry dimethylformamide (300 ml) was stirred at 23° C. for 20 hours. The solvent was evaporated under reduced pressure and the residue dissolved in tetrahydrofuran: diethyl ether (1:1) solution (150 ml) and left at −20° C. for 12 hours. The precipitate was collected by filtration, washed with tetrahydrofuran:diethyl ether (1:1) solution and the combined solutions were evaporated to an oil (5.06 g). The crude product was dissolved in 80% acetic acid (120 ml) and stirred at 40° C. for 2 hours. The acid was then evaporated under reduced pressure and the residue coevaporated with toluene (3×50 ml). The product was purified by column chromatography on silica gel (eluting with dichloromethane:ethanol 97:3) to give the title compound (1.75 g, 47%). $^1$H NMR: $\delta_H$ [(CD$_3$)$_2$SO] 0.04 (6H, s, (CH$_3$)$_2$Si)), 0.85 (9H, s, (CH$_3$)$_3$C), 1.21 (6H, t, (CH$_3$CH$_2$O)$_2$), 1.62 (4H, m, CHCH$_2$CH$_2$P), 3.26 (2H, m, CH$_2$OH), 3.64 (1H, m, CHCH$_2$CH$_2$P), 3.96 (4H, m, (CH$_3$CH$_2$O)$_2$), 4.63 (1H, t, D$_2$O exchangeable, CH$_2$OH). Found: C, 48.94; H, 9.98%. C$_{14}$H$_{33}$O$_5$PSi 0.3 H$_2$O requires: C, 48.62; H, 9.79%.

g) 2-(N,N-Bis-tert-butoxycarbonyl)amino-6-methoxy-9-[2-tert-butyldimethylsilyloxy)-4-(diethoxyphosphoryl)butoxy]purine To a solution of 2-(N,N-bis-tert-butoxycarbonyl)amino-6-methoxy-9-hydroxypurine (0.280 g, 0.735 mmol), diethyl [3-(tert-butyldimethylsilyloxy)-4-hydroxybutyl]phosphonate (0.250 g, 0.735 mmol) and triphenylphosphine (0.290 g, 1.025 mmol) in dry tetrahydrofuran (25 ml) at 0° C., diethyl azodicarboxylate (1.74 ml, 1.10 mmol) was added. The resulting reaction mixture was stirred at 0° C. for 25 minutes it was then allowed to warm to room temperature and stirred for an additional 2 hours. The solvent was evaporated under reduced pressure and the residue redissolved in diethyl ether and left at −20° C. for 12 hours. The resulting crystalline material was filtered, washed with diethyl ether and the combined solutions evaporated to an oil. The product was purified by column chromatography on silica gel (eluting with dichloromethane:ethanol 98:2) to give the title compound (0.418 g, 81%). $^1$H NMR: $\delta_H$ (CDCl$_3$) 0.09 (6H, d, (CH$_3$)$_2$Si), 0.9 (9H, m, (CH$_3$)$_3$C), 1.33 (6H, t, (CH$_3$CH$_2$O), 1.45 (18H, s, t-BOC), 1.87 (4H, m, CHCH$_2$CH$_2$P), 4.11 (8H, m, OCH$_3$, (CH$_3$CH$_2$O)$_2$, CHCH$_2$CH$_2$P), 4.33 (2H, m, OCH$_2$), 8.07 (1H, s, H-8). Found: C,50.90; H, 7.87; N,9.72%. C$_{30}$H$_{54}$N$_5$O$_{10}$PSi 0.4 H$_2$O requires: C,50.67; H,7.77; N,9.85%.

h) 6-O-Methyl-9-[2-hydroxy-4-(diethoxyphosphoryl)-butoxy]guanine

A solution of 2-(N,N-bis-tert-butoxycarbonyl)amino-6-methoxy-9-[2-tert-butyldimethylsilyloxy)- 4-diethoxyphosphoryl)butoxy]purine (0.370 g, 0.53 mmol) in 80% acetic acid (20 ml) was stirred at 80° C. for 10 hours. The solvent was then evaporated and the residue evaporated with toluene (2×30 ml). The product was purified by column chromatography on silica gel (eluting with chloroform:ethanol 91:9) to give the title compound (0.165 g, 78%). $^1$H NMR: $\delta_H$ [(CD$_3$)$_2$SO] 1.21 (6H, m, (CH$_3$CH$_2$O)$_2$), 1.7 (4H, m, CHCH$_2$CH$_2$P), 3.75 (1H, m, CHCH$_2$CH$_2$P), 3.95 (7H, m, OCH$_3$, (CH$_3$CH$_2$O)$_2$, 4.16 (2H, m, OCH$_2$), 5.28 (1H, d, D$_2$O exchangeable, CHOH) 6.62 (2H, br.s, D$_2$O exchangeable, NH$_2$), 8.08 (1H, s, H-8).

DESCRIPTION 9

(Intermediates for Examples 14 and 15)

a) 9-Benzyloxy-6-chloropurine

A mixture of 4,6-dichloro-5-formamidopyrimidine (58.6 g; 0.31 mmol), benzyloxyamine (37.5 g; 0.31 mmol), triethylamine (110 ml) and dioxan (400 ml) was stirred at 100° C. for 4 hours. The reaction was cooled, filtered and evaporated under reduced pressure. The residue was partitioned between ethyl acetate (750 ml), saturated aqueous potassium bicarbonate (400 ml) and brine (200 ml). The organic phase was separated and the aqueous phase washed with ethyl acetate (300 ml). The combined organic phases were washed with water (200 ml), brine (200 ml), dried (MgSO$_4$), and evaporated under reduced pressure.

The residue was dissolved in anhydrous N,N-dimethyl-formamide (100 ml), triethyl orthoformate (200 ml), and 12N hydrochloric acid (5 ml). After 4 hours at 25° C. the solvent was removed under reduced pressure. The residue was partitioned between chloroform (750 ml) and saturated aqueous potassium bicarbonate (500 ml). The resulting suspension was filtered and the phases separated. The organic phase was washed with saturated potassium bicarbonate (200 ml), water (200 ml), dried (MgSO$_4$) and evaporated under reduced pressure. The residue was purified by column chromatography on silica gel eluting with chloroform-methanol (100:1), affording the title compound (38.4 g, 48). IR: $\upsilon_{max}$ (KBr) 3350, 1587, 1565, 1438 cm$^{-1}$; $^1$H NMR: $\delta_H$ (CDCl$_3$) 5.40(2H, s, CH$_2$Ar), 7.35(5H, s, Ar), 7.75(1H, s, H-8), 9.85(1H, s, H-2). Found: C, 55.11; H, 3.73; N, 21.27%. C$_{12}$H$_9$N$_4$OCl requires: C, 55.28; H, 3.49, N, 21.50%.

b) 9-Benzyloxyadenine

A solution of 9-benzyloxy-6-chloropurine (38.4 g; 0.147 mmol) in ethanol (300 ml) saturated with ammonia was heated at 100° C. in an autoclave for 16 hours. After cooling the suspension was evaporated to dryness and the residue partitioned between chloroform (750 ml) and water (500 ml). The separated aqueous phase was washed with chloroform (200 ml). The combined organic phases were washed with water, dried (MgSO$_4$) and evaporated, affording an orange solid homogeneous on t.l.c. (31.1 g, 87%). IR: $\upsilon_{max}$ (KBr) 3372, 3300, 3187, 3038, 1660, 1637, 1600, 1581 cm$^{-1}$; $^1$H NMR: $\delta_H$ [(CD$_3$)$_2$SO] 5.3(2H, s, CH$_2$Ar), 6.8(2H, br.s, D$_2$O exchangeable, NH$_2$), 7.3(6H, s, H-8, Ar), 7.7(1H, s, H-2). Found: C, 59.39; H, 4.60; N, 29.07%; m/e 241.0949. C$_{12}$H$_{11}$N$_5$O requires: C, 59.73; H, 4.60; N, 29.03%; m/z 241.0964.

c) 9-Benzyloxy-6-phthalimidopurine

Phthaloyl dichloride (13.35 g; 92.2 mmol) was added to a cooled solution of 9-benzyloxyadenine (14.9 g, 61.5 mmol), 4-dimethylaminopyridine (1.5 g, 12.3 mmol) and triethylamine (25.7 ml, 184.4 mmol) in tetrahydrofuran (200 ml). After 1 hour at room temperature the solvent was removed under reduced pressure and the residue partitioned between chloroform (500 ml) and saturated potassium bicarbonate (300 ml). The organic phase was separated, washed with water (200 ml), brine (200 ml), dried (MgSO$_4$) and evaporated to dryness. Column chromatography on silica gel eluting with chloroform-methanol (100:1) afforded the title compound (11.20 g, 49%). IR: $\upsilon_{max}$ (KBr) 3070, 1800, 1740, 1730, 1605, 1585, 1450 and 1410 cm$^{-1}$; $^1$H NMR $\delta_H$ [(CD$_3$)$_2$SO] 5.70(2H, s, CH$_2$Ph), 7.55(5H, s, CH$_2$Ph), 8.20(4H, s, Ar), 8.95(1H, s, H-2), 9.25(1H, s, H-8). Found: C, 64.71; H, 3.78; N, 18.85%; m/z 371.1025. C$_{20}$H$_{13}$N$_5$O$_3$ requires: C, 64.68; H, 3.54; N, 18.86%; m/e 371.1018.

d) 9-Hydroxy-6-phthalimidopurine

A mixture of 9-benzyloxy-6-phthalimidopurine (11.0 g, 29.5 mmol), 10% palladium on charcoal (2.2 g), ethanol (300 ml) and tetrahydrofuran (500 ml) was stirred at 25° C. for 1 hour under an atmosphere of hydrogen. The suspension was then filtered and the catalyst washed with ethanol. The filtrate was evaporated under reduced pressure and the resulting solid triturated with ether. The solid was collected and then dried to afford the title compound (6.93 g; 83%). IR: $\upsilon_{max}$ (KBr). 2607, 1794, 1735, 1603, 1582, 1467, 1401 cm$^{-1}$; $^1$H NMR $\delta_H$ [(CD$_3$)$_2$SO] 8.15(4H, s, Ar), 8.95(1H, s, H-2), 9.15(1H, s, H-8), 12.80(1H, br.s, D$_2$O exchangeable, OH). Found:

C, 55.34; H, 2.58; N, 24.56%. $C_{13}H_7N_5O_3$ requires: C, 55.51; H, 2.51; N, 24.91%.

e) 6-Phthalimido-9-[2-(2-(tert-butyldimethyl-silyloxy)-4-(diethoxyhosphoryl)butoxy]purine To a solution of 9-hydroxy-6-phthalimidopurine (0.185 g, 0.656 mmol), diethyl[3-(tert-butyldimethylsilyloxy)-4-hydroxybutyl]phosphonate (0.220 g, 0.656 mmol) and triphenylphosphine (0.257 g, 0.984 mmol) in dry tetrahydrofuran (20 ml) at 0° C., diethyl azodicarboxylate (1.54 ml, 0.984 mmol) was added. The reaction mixture was stirred at 0° C. for 25 minutes; it was the allowed to warm to room temperature and stirred for additional 2 hours. The solvent was evaporated and the residue redissolved in diethyl ether and left at −20° C. for 5 hours. The resulting crystalline material was filtered, washed with diethyl ether and the combined solutions evaporated to an oil. The product was purified by column chromatography on silica gel (eluting with dichloromethane:ethanol 98:2) to give the title compound (0.340 g, 86). $^1H$ NMR: $\delta_H$ (CDCl$_3$) 0.12 (6H, d, (CH$_3$)$_2$Si), 0.91 (9H, s, (CH$_3$)$_3$C), 1.34 (6H, t, (CH$_3$CH$_2$O)$_2$), 1.92 (4H, m, CHC$\underline{H_2}$C$\underline{H_2}$P), 4.16 (5H, m, (C$\underline{H_3}$CH$_2$O)$_2$, CHCH$_2$CH$_2$P), 4.45 (2H, m, CH$_2$O), 7.95 (4H, m, phthaly$\underline{l}$, protons), 8.31 (1H, s, H-2), 9.07 (1H, s, H-8). Found: C, 52.57; H,6.45; N, 11.35%.

f) 9-2-tert-Butyldimethylsilyloxy)-4-(diethoxy-phosphoryl)butoxy]adenine

A solution of 6-phthalimido-9-[2-(tert-butyldimethylsilyloxy)-4-(diethoxyphosphoryl)butoxy]purine (0.290 g, 0.48 mmol) and methylhydrazine (0.03 ml, 0.58 mmol) in dry dichloromethane (15 ml) was stirred at room temperature for 1.5 hour; the precipitate was then filtered, washed with dichloromethane and the combined solutions were evaporated under reduced pressure. The product was purified by column chromatography on silica gel (eluting with dichloromethane:ethanol 96:4) to give the title compound as a colorless glass which was crystallized from ethanol:diethyl ether (193 mg, 85%); mp. 98° C. $^1H$ NMR: $\delta_H$ [(CDCl$_3$)$_2$SO] 0.06 (6H, s, (CH$_3$)$_2$Si), 0.84 (9H, s, (CH$_3$)$_3$C), 1.23 (6H, t, (CH$_3$CH$_2$O)$_2$), 1.83 (4H, m, CHC$\underline{H_2}$C$\underline{H_2}$P), 3.99 (4H, m, (C$\underline{H_3}$CH$_2$O)$_2$), 4.12 (1H, m, C$\underline{H}$CH$_2$CH$_2$P), 4.32 (2H, d, OC$\underline{H_2}$), 7.36 (2H, br.s, D$_2$O exchangeable, NH$_2$), 8.14 (1H, s, H-2), 8.35 (1H, s, H-8). Found: C, 46.77; H,7.79; N, 14.73%. $C_{19}H_{36}N_5O_5PSi$ 0.8H$_2$O requires: C, 46.92; H, 7.79; N, 14.4%.

DESCRIPTION 10

(Intermediate for Example 16)

2-Amino-9-[3-(diethoxyphosphoryl)-1-(hydroxymethyl)-propoxy]-6-methoxypurine

Diethyl azodicarboxylate (0.43 ml, 2.75 mmol) was added to a cooled mixture of 2-[bis-(t-butoxycarbonyl)-amino]-9-hydroxy-6-methoxypurine (0.71 g, 1.83 mmol), triphenylphosphine (0.72 g, 2.75 mmol) and diethyl 4-(t-butyldimethylsilyloxy)-3-hydroxybutylphosphonate (0.623 g, 1.83 mmol) in dry tetrahydrofuran (20 ml). The reaction mixture was stirred at ambient temperature for 1 hour, and then evaporated to dryness. The residue was dissolved in diethyl ether, the solution filtered, and the filtrate evaporated to give a yellow oil. This oil was partially purified by column chromatography on silica gel (eluting with dichloromethane:ethanol 97:3) to give 2-[bis-(t-butoxycarbonyl)amino]-9-[1-(t-butyldimethylsilyloxymethyl)-3-(diethoxyphosphoryl)-propoxy]-6-methoxypurine as a yellow oil (1.20 g, 98%).

This was then dissolved in 80% acetic acid (60 ml), heated to 80° C. and stirred for 2 hours. The reaction mixture was allowed to cool and the solution evaporated to dryness. The resulting oil was coevaporated with toluene (3 × 30 ml) and the product was purified by column chromatography on silica gel (eluting with chloroform: ethanol 95:5) to give the title compound as an oil (537 mg, 81%). $^1H$ NMR: $\delta_H$[(CD$_3$)$_2$SO] 1.22 (6H, t, J=7Hz, (OCH$_2$CH$_3$)$_2$), 1.78-2.08 (4H, m, CH$_2$CH$_2$P), 3.53-3.61 (2H, m, C$\underline{H_2}$OH), 3.96 (3H, s, OCH$\underline{H_3}$), 3.85-4.07 (4H, m, (OC$\underline{H_2}$CH$_3$)$_2$), 4.26-4.33 (1H, m, NOCH), 5.06 (1H, t, J=6Hz, D$_2$O exchangeable OH), 6.61 (2H, br.s, D$_2$O exchangeable NH$_2$), 8.06 (1H, s, H-8).

DESCRIPTION 11

(Intermediates for Example 17)

a) 1-Bromo-2,3-di-(t-butyldimethylsilyloxy)propane

A solution of 1-bromopropanediol (25 g, 161.3 mmol), t-butyldimethylsilyl chloride (53.2 g, 354.9 mmol) and imidazole (48.3 g, 709.72 mmol) in dimethylformamide (370 ml) was stirred at 23° C. for 24 hours. The solvent was then evaporated under reduced pressure, the residue was redissolved in diethyl ether:dichloromethane (1:1, 400 ml) and left at −20° C. for 12hours. The precipitate was collected by filtration, washed with diethyl ether:dichloromethane (1:1) and the combined filtrates were evaporated to give the title compound as a virtually pure oil. (55 g, 89%). $^1H$ NMR: $\delta_H$(CD$_3$)$_2$SO] 0.005 (12H, m, (CH$_3$)$_2$Si), 0.82 (18H, s, (CH$_3$)$_3$C), 3.45 (4H, m, CH$_2$Br, CH$_2$O), 3.79 (1H, m, CH). m/z: (C.I., NH$_3$), 402 (M NH$_4^+$ 100), 385 (MH$^+$, 68%); found: 383.1439 (M+). $C_{15}H_{35}O_2Br$ requires: 383.1473 (M+). A sample of the material was purified by short column chromatography on silica gel (eluting with 5% ethyl acetate in hexane) to give an analytical sample. Found: C,44.79; H,8.48, $C_{15}H_{35}O_2Br$ H$_2$O requires: C,44.86; H,9.28%.

b) Diethyl 2,3-di(t-butyldimethylsilyloxy)propylphosphonate

Triethyl phosphite (28 ml, 163.25 mmol) and 1-bromo-2,3-di-(t-butlyldimethylsilyloxy)propane (25 g, 65.2 mmol) were stirred together at 130° C. for 72 hours. The reaction mixture was allowed to cool and the excess triethylphosphite was removed by distillation under reduced pressure. The product distilled at 120° C./0.5mm Hg. Yield: 15.5 g (54%). 1H NMR: $\delta_H$[(CD$_3$)$_2$SO] 0.04 (12H,m, (CH$_3$)$_2$Si), 0.86 (18H, d, (CH$_3$)$_3$C), 1.22 (6H, t, (CH$_3$CH$_2$O)$_2$), 1.92 (2H, m, CH$_2$P), 3.47 (2H, m, CH$_2$O), 3.96 (5H, m, (CH$_3$CH$_2$O)$_2$, C$\underline{H}$). Found: C,51.84; H,10.41. $C_{19}H_{45}O_5SiO_2P$ requires: C,51.78; H,10.29%. m/z:(C.I., NH$_3$) 441 (MH$^+$, 100). c) Diethyl 2-(t-butyldimethylsilyloxy)-3-hydroxypropylphosphonate A solution of diethyl 2,3-di-(t-butyldimethylsilyloxy)-propylphosphonate (5 g, 11.35 mmol) in 80% acetic acid (150 ml) was stirred at 40° C. for 3 hours. The acid was evaporated under reduced pressure and the residue coevaporated with toluene: ethanol solution (3 × 50 ml). The crude product was purified by column chromatography on silica gel (eluting with chloroform:ethanol, 97:3) to give the title compound as a colorless solid (1.44 g, 39%) m.p. 35°-40° C. $^1H$ NMR: $\delta_H$[(CD$_3$)$_2$SO] 0.008 (6H, 2xs, (CH$_3$)$_2$Si), 0.79 (9H, s, (CH$_3$)$_3$C), 1.16 (6H, t, (CH$_3$CH$_2$O)$_2$), 1.86 (2H, m, PCH$_2$), 3.27 (3H, m, PC$\underline{H_2}$CHCH$_2$), 3.89 (4H, m, (CH$_3$C$\underline{H_2}$O)$_2$), 4.65 (1H, t, D$_2$O$_3$ exchangeable OH). Found: C,47.35; H,9.67%. C$_{13}$H$_{31}$O$_5$PSi 0.2 H$_2$O requires: C,47.31; H, 9.59%.

d) 2-[(N,N-bis-t-bis-t-butyoxycarbonyl)amino]-6-methoxy-9-[2-(t-butyldimethylsilyloxy)-3-(diethoxyphosphoryl)propoxy]purine To a solution of 2-[(N,N-bis-t-bis-t-butyoxycarbonyl)-amino]-6-methoxy-9-hydroxypurine (0.453 g, 1.19 mmol), diethyl-2-(t-butyldimethylsilyloxy)-3-hydroxypropyl-phosphonate (0.390 g, 1.19 mmol) and triphenylphosphine (0.470 g, 1.79 mmol) in tetrahydrofuran (25 ml) at 0° C., was added diethyl azodicarboxylate (0.28 ml, 1.79 mmol). The resulting reaction mixture was stirred at 0° C. for 25 minutes; it was then allowed to warm to room temperature and stirred for an additional 1 hour. The solvent was removed under reduced pressure and the residue redissolved in diethyl ether:hexane (6:4) solution. The resulting crystalline material was filtered off, the filtrate evaporated under reduced chromatography on silica gel (eluting with 2% ethanol in dichloromethane) to give the title compound as an oil (0.76 and 93). $^1$H NMR: $\delta_H$(CDCl$_3$) 0.11, (6H, 2xs, (CH$_3$)$_2$Si), 0.88 (9H, s, (CH$_3$)$_3$C), 1.34 (6H, t, (CH$_3$CH$_2$O)$_2$), 1.45 (18H, s, 2xt-BOC), 2.23 (2H, m, PCH$_2$), 4.13 (7H, m, CH$_3$O, (CH$_3$CH$_2$O)$_2$, 4.49 (3H, m, PCH$_2$CHCH$_2$), 8.14 (1H, s, H-8). Found: C,49.20; H,7.53; N,9.92%. C$_{29}$H$_{52}$N$_5$O$_{10}$PSi 1H$_2$O requires: C,49.21; H,7.68; N,9.89%.

e) 2-Amino-6-methoxy-9-[2-hydroxy-3-(diethoxyphosphoryl)propoxy]purine

To a solution of 2-[(N,N-bis-t-bis-t-butyoxycarbonyl)-amino]-6-methoxy-9-[2-(t-butyldimethylsilyloxy)-3-(diethoxyphosphoryl)]purine (0.3 g, 0.435 mmol) in 80% acetic acid was stirred at 80° C. for 8 hours. The solvent was removed under reduced pressure and the residue coevaporated with toluene:chloroform (1:1) solution (3×50 ml). The crude product was chromatographed on silica gel column (eluting with 5% ethanol in chloroform) to give the title compound as an oil (0.110 g, 66%). $^1$H NMR: $\delta_H$[(CDCl$_3$)$_2$SO] 1.19 (6H, m, (CH$_3$CH$_2$O$_2$)$_2$), 2.0 (2H, m, PCH$_2$), 3.96 (3H, s, CH$_3$O), 4.13 (7H, m, CH$_3$CH$_2$O)$_2$, PCH$_2$CH$_2$CH$_2$), 5.51 (1H, d, D$_2$O exchangeable OH), 6.63 (2H, br.s, D$_2$O exchangeable NH$_2$), 8.10 (1H, s, H-8). Found: C,41.19; H,6.02; N,18.45%. C$_{13}$H$_{22}$N$_5$O$_6$P requires: C,41.60; H,5.91; N,18.65%.

DESCRIPTION 12

(Intermediates for Examples 18, 19 and 20)

a) Diethyl 4-acetoxy-3-(acetoxymethyl)butylphosphonate

Triethyl phosphite (6.58 g, 6.8 ml, 39.67 mmol) and 4-acetoxy-3-(acetoxymethyl)butyl iodide (5 g, 15.87 mmol) were stirred at 130° C. for 9 hours. The reaction mixture was then allowed to cool and the excess of triethyl phosphite was evaporated under reduced pressure. The product distilled at 235° C./0.3 mm Hg, yield 4.6 g, 75%. $^1_H$NMR: δH (CDCl$_3$) 1.33 (6H, t, J=7Hz, (OCH$_2$CH$_3$)$_2$), 1.74 (5H, m, CHCH$_2$CH$_2$P), 2.06 (6H, s, 2xCOCH$_3$), 4.12 (8H, m, (OCH$_2$CH$_3$)$_2$, 2xCH$_2$OAc). Found: C,47.29; H,7.83%. C$_{13}$H$_{25}$O$_7$P 0.25 H$_2$O requires C,47.48; H,7.81%.

b) Diethyl 4-hydroxy-3-(hydroxymethyl)butyl-phosphonate

Diethyl 4-acetoxy-3-(acetoxymethyl)butylphosphonate (4.6 g, 14.18 mmol) was dissolved in hydrochloric acid/ethanol solution (14 ml, 2.2M) and the reaction mixture was stirred at 80° C. for 90 minutes. It was then cooled to 5° C., neutralized with aqueous ammonia solution and diluted with tetrahydrofuran. The resulting ammonium hydrochloride was filtered off, washed with tetrahydrofuran and the combined filtrates concentrated to an oil which was chromatographed on silica gel (eluting with 94:6 CHCl$_3$:EtOH) to give the title compound (2.1 g, 62%). $^1$H NMR $\delta_H$ ](CD$_3$)$_2$SO] 1.22 (6H, t, 7=7Hz, (OCH$_2$CH$_3$)$_2$), 1.46 (3H, m, CH$_2$CH) 1.72 (2H, m, PCH$_2$), 3.35 (4H, m, 2xH$_2$OH), 3.5–3.75 (2H, br.s, D$_2$O exchangeable, 2xOH), 3.96 (4H, m, (OCH$_2$CH$_3$)$_2$). Found: C,44.79: H,8.93%. C$_9$H$_{21}$O$_5$P 0.2 H$_2$O requires: C,44.43; H,8.86.

DESCRIPTION 13

(intermediates for Examples 18, 20)

a) Diethyl 4-acetoxy-3-(hydroxymethyl)butylphosphonate

Diethyl 4-hydroxy-3-(hydroxymethyl)butylphosphonate (0.28 g, 1.16 mmol) trimethyl orthoacetate (0.381 ml, 3 mmol) and trifluoroacetic (0.1 ml, 1.3 mmol) in acetonitrite (5 ml) were stirred at 23° C. for 4 hours. Water (1 ml) was added and the reaction mixture was stirred for an additional 20 minutes. The solution was neutralized with aqueous ammonia to pH=7.0 and the solvents were evaporated under reduced pressure. The residue was chromatographed on silica gel (eluting with 97:3 CHCl$_3$:EtOH) to give the title compound (0.280 g, 85%). $^1$H NMR: $\delta_H$ [(CD$_3$)$_2$SO] 1.22 (6H, t, J=7Hz, (OCH$_2$CH$_3$)$_2$), 1.46 (2H, m, PCH$_2$), 1.75 (3H, m, PCH$_2$CH$_2$CH), 2.0 (3H, s, COCH$_3$), 3.35 (2H, m, CH$_2$OH), 3.97 (6H, m, CH$_2$OAc, (OCH$_2$CH$_3$)$_2$), 4.57 (1H, t, J=5Hz, D$_2$O exchangeable, CH$_2$OH). Found: C,44.61; H,8.35%. C$_{11}$H$_{23}$O$_6$P 0.75 H$_2$O requires: C,44.66; H,8.34%.

b) Diethyl 3-(acetoxymethyl)-4-(N-phthalimodooxy)-butylphosphonate

To a cooled solution of diethyl 4-acetoxy-3-(hydroxymethyl)butylphosphonate (0.760 g, 2.68 mmol), diethyl azodicarboxylate (0.513 g, 2.95 mmol) and N-hydroxyphthalimide (0.437 g, 2.68 mmol) in dry tetrahydrofuran (25 ml) was added triphenylphosphine (0.78 g, 2.95 mmol). The reaction mixture was stirred at 23° C. for 6 hours and the solvent was evaporated. The residue was dissolved in diethyl ether and the resulting solution was stirred at 0° C. for 2 hours. Triphenylphosphine oxide was filtered off, washed with diethyl ether and the combined diethyl ether solutions were evaporated to dryness. The residual oil was purified by column chromatography on silica gel (eluting with chloroform) to give the title compound (0.85 g, 74%). $^1$H NMR: $\delta_H$ (CDCl$_3$) 1.34 (6H, t, J=7Hz, (OCH$_2$CH$_3$)$_2$, 1.87 (4H, m, CH$_2$CH$_2$P), 2.09 (3H, s, COCH$_3$), 2.24 (1H, m, CH), 4.16 (8H, m, (OCH$_2$CH$_3$)$_2$, CH$_2$OAc, NOCH$_2$), 7.79 (4H, m, phthalyl protons). Found: C,52.67; H,6.3; N,2.48%. C$_{19}$H$_{26}$NO$_8$P 0.5 H$_2$O requires: C,52.29; H,6.23; N,3.20%.

c) Diethyl 3-(acetoxymethyl)-4-(aminooxy)butylphosphonate

To a solution of diethyl 3-(acetoxymethyl)-4-(N-phthalimidooxy)butylphosphonate (1.0 g, 2.3 mmol) in dry dichloromethane (25 ml) was added methylhydrazine (0.13 ml, 0.113 g, 2.415 mmol). The reaction mixture was stirred at 23° C. for 1 hour, the precipitate filtered off, washed with dichloromethane and the combined solvents evaporated to dryness. The product was purified by column chromatography on silica gel (eluting with chloroform:ethanol 98:2) to give the title compound as a colorless oil (0.460 g, 66%). $^1$H NMR: $\delta_H$

[(CD$_3$)$_2$SO] 1.22 (6H, t, J=7Hz, (OCH$_2$CH$_3$)$_2$), 1.5 (2H, m, CHCH$_2$CH$_2$), 1.75 (2H, m, CH$_2$P), 2.0 (4H, s, COCH$_3$, CHCH$_2$), 3.5 (2H, m, CH$_2$OAc), 4.0 (6H, m, NOCH$_2$, (OCH$_2$CH$_3$)$_2$), 6.0 (2H, s, D$_2$O exchangeable NH$_2$). Found: C,44.36; H,8.53; N,4.55%. C$_{11}$H$_{24}$NO$_6$P requires: C,44.44 H,8.14; N,4.71%.

d) 4-Chloro-6-[2-(acetoxymethyl)-4-(diethoxyphosphoryl)butoxyamino] 2,5-diformamidopyrimidine 4,6-Dichloro-2,5-diformamidopyrimidine (0.390 g, 1.66 mmol), diethyl 3-(acetoxymethyl)-4-(aminooxy)-butylphosphonate (0.380 g, 1.275 mmol) and N,N-diisopropylethylamine (0.58 ml, 3.22 mmol) were dissolved in diglyme (15 ml) and the resulting mixture was stirred at 100° C. for 3 hours. The reaction mixture was then allowed to cool, N,N-diisopropylethylamine hydrochloride was filtered off and the filtrate was evaporated to dryness. The residue was chromatographed on silica gel (eluting with chloroform:ethanol 97:3) to give the title compound (0.480 g, 76%). $^1$H NMR: $\delta_H$ [(CD$_3$)$_2$SO] 1.22 (6H, t, J=7Hz (OCH$_2$CH$_3$), 1.75 (4H, m, CH$_2$CH$_2$P), 2.01 (4H, m, COCH$_3$, CHCH$_2$) 4.0 (8H, m, CH$_2$OAc, NOCH$_2$, (OCH$_2$)$_2$) 8.15 (1H, s, 5-NHCHO), 9.25 (1H, s, 2-NHCHO), 9.40 (1H, br.s, D$_2$O exchangeable, NHOCH$_2$) 10.80 (2H, br.s. D$_2$O exchangeable, 2x NHCHO). Found: C,41.97, H,5.80; N,13.17%. C$_{17}$H$_{27}$N$_5$O$_8$PCl requires: C,41.17; H,5.49; N,14.12%.

e) 6-Chloro-9-[2-(acetoxymethyl)-4-(diethoxyphosphoryl)butoxy]-2-formamidopurine 4-Chloro-6-[2-(acetoxymethyl)-4-(diethoxyphosphoryl) butoxyamino]-2,5-diromamidopyrimidine (0.170 g, 0.343 mmol) in diethoxymethylacetate (5 ml) was stirred at 120° C. for 2.5 hours. The reaction mixture was allowed to cool and excess diethoxymethylacetate was removed under reduced pressure. The residue was dissolved in methanolic ammonia (2M)(5 ml) and stirred at 23° C. for 10 minutes. The solvents were evaporated under vacuum and the product was purified by column chromatography on silica gel (eluting with chloroform-;ethanol 99:1) to give the title compound (0.128 g, 79%. $^1$H NMR: $\delta_H$ (CDCl$_3$) 1.2 (6H, t, (OCH$_2$CH$_3$)$_2$), 1.75 (4H, m, CH$_2$CH$_2$, P), 2.0 (3H, s, COCH$_3$), 2.2 (1H, m, CHCH$_2$) 4.0 (4H, m, (OCH$_2$CH$_3$)$_2$), 4.2 (2H, m, CH$_2$OAc), 4.3 (2H, m, NOCH$_2$) 8.2 (1H, s, H-8), 9.6 (2H, br.s. NHCHO, D$_2$O exchangeable NHCHO).

DESCRIPTION 14

(Intermediate for Example 18)

9-[2-(Hydroxymethyl)-4-(diethoxyphosphoryl)butoxy]guanine

A solution of 6-chloro-9-[2-(acetoxymethyl)-4-(diethoxyphosphoryl)butoxy]-2-formamidopurine (0.128 g, 0.268 mmol) in 80% formic acid (5 ml) was stirred at 80° C. for 5 hours. The solvent was evaporated under reduced pressure and the residue coevaporated with toluene (2×10 ml). The residue was redissolved in a 0.02 M solution of hydrochloric acid in ethanol (4ml) and the resulting mixture stirred at 90° C. for 2 hours. The solvents were evaporated under reduced pressure and the residue coevaporated with ehtanol (2×15 ml). The product was purified by column chromatography on silica gel (eluting with chloroform:ethanol 92:8) to give the title compound (64 mg, 61%). $^1$H NMR $\delta_H$ [(CD$_3$)SO] 1.22 (6H, t, J=7Hz, (CH$_3$CH$_2$O)$_2$), 1.75 (5H, m, CHCH$_2$CH$_2$P), 3.5 (2H, m, CH$_2$OH), 4.0 (4H, m, (OCH$_2$CH$_3$)$_2$), 4.24 (2H, m, NOCH$_2$), 4.64 (1H, t, J=5.2Hz, D$_2$O exchangeable, CH$_2$OH), 6.55 (2H, br.s, D$_2$O exchangeable, NH$_2$), 7.92 (1H, s, H-8), 10.52 (1H, br.s, D$_2$O exchangeable, NH).

DESCRIPTION 15

(Intermediate for Example 20)

2,6-Diamino-9-[2-(hydroxymethyl)-4-(diethoxyphosphoryl)butoxy]purine

6-Chloro 9-[2-(acetoxymethyl)-4-(diethoxyphosphoryl)-butoxy]-2-formamidopurine (0.110 g, 0.23 mmol) was dissolved in ethanolic ammonia solution (5 ml) and the resulting reaction mixture was kept at 110°0 C. for 6 hours. The solution was allowed to cool, the solvent was evaporated and the residue chromatographed on silica gel (eluting with chloroform 9:1) to yield the title compound (40 mg, 45%). $^1$H NMR: $\delta_H$ [(CD$_3$)$_2$SO] 1.22 (6H, t, (OCH$_2$CH$_3$)2), 1.76 (5H, m, CHCH$_2$CH$_2$P), 3.49 (2H, br.s, CH$_2$OH), 3.99 (4H, m, (OCH$_2$CH$_3$)$_2$), 4.25 (2H, m, NOCH$_2$), 4.72 (1H, br.s, D$_2$O exchangeable CH$_2$OH), 5.9 (2H, br.s, D$_2$O exchangeable, NH$_2$), 6.79 (2H, br.s, D$_2$O exchangable, NH$_2$), 8.31 (1H, s, H-8).

DESCRIPTION 16

(Intermediates for Example 19)

a) Diethyl 4-(t-butyldimethylsilyloxy)-3-(hydroxymethyl)butylphosphonate

Diethyl 4-hydroxy-3-(hydroxymethyl)butylphosphonate (2.15 g, 8.95 mmol) t-butyldimethylsilyl chloride (1.47 g, 9.84 mmol) and imidazole (1.34 g, 19.7 mmol) in dry dimethylformamide (40ml) were stirred at 23° C. for 8 hours. The solvent was evaporated under reduced pressure and the residue dissolved in chloroform (250 ml). The resulting solution was washed with sat.aq. NaHCO$_3$ (2×30ml), the solvent evaporated under reduced pressure and the product purified by column chromatography on silica gel (eluting with chloroform:ethanol 98:2) to give the title compound (1.0 g, 32). $^1$H NMR: $\delta_H$(CDCl$_3$) 0.07 (6H, s, (CH$_3$)$_2$Si), 0.89 (9H, s, (CH$_3$)$_3$C), 1.32 (6H, t, (OCH$_2$CH$_3$), 1.72 (5H, m, PCH$_2$CH$_2$CH), 2.77 (1H, br.s, D$_2$O exchangeable, CH$_2$OH), 3.7 (4H, m, CH$_2$OH, CH$_2$OTBDMS), 4.09 (4H, m, (OCH$_2$CH$_3$)$_2$). Found: C, 48.98; H, 10.07%. C$_{15}$H$_{35}$O$_5$SiP H$_2$O requires: C,48.37; H,10.02%.

b) Diethyl 3-(t-butyldimethylsilvloxymethyl)-4-(N-phthalimidooxy)butylphosphonate To a cooled solution of diethyl 4-(t-butyldimethylsilyloxy)-3-(hydroxymethyl)butyl-phosphonate (0.747 g, 2.1 mmol), diethyl azodicarboxylate (0.364 ml, 2.31 ml) and N-hydroxyphthalimide (0.342 g, 2.1 mmol) in dry tetrahydrofuran (25 ml) was added triphenylphosphine (0.605 g, 2.31 mmol). The reaction mixture was stirred at 23° C. for 3 hours, and the solvent was evaporated. The residue was redissolved in diethyl ether and the resulting solution was stirred at 0° C. for 2 hours. Triphenylphosphine oxide was filtered off and washed with diethyl ether. The combined diethyl ether solutions were evaporated to dryness and the product was purified by column chromatography on silica gel (eluting with chloroform) to give the title compound (0.73 g, 70%). $^1$H NMR: $\delta_H$(CDCl$_3$) 0.07 (6H, s, (CH$_3$)$_2$Si), 0.88 (9H, s, (CH$_3$)$_3$C), 1.33 (6H, t, (OCH$_2$CH$_3$)$_2$, 1.88 (5H, m, PCH$_2$CH$_2$CH) 3.75 (2H, m, CH$_2$OTBDMS), 4.16 (6H, m, (OCH$_2$CH$_3$)$_2$, NOCH$_2$), 7.55 (4H, m, phthalyl protons). Found: C, 54.38; H, 7.93; N,2.11%. C$_{23}$H$_{39}$NO$_7$PSi 0.6 H$_2$O requires: C, 54.12; H, 7.93; N, 2.74.

c) Diethyl 3-(t-butyldimethylsilyloxymethyl)-4-(aminooxy)butylphosphonate

To a solution of diethyl 3-(t-butyldimethylsilyloxymethyl)-4-(N-phthalimidooxy)butylphosphonate (0.68 g, 1.36 mmol) in dry dichloromethane (20 ml) was added methylhydrazine (0.07 g, 1.36 mmol). The reaction mixture was stirred at 23° C. for 1 hour. The precipitate was filtered off, washed with dichloromethane and the combined solvents were evaporated to dryness. The product was purified by column chromatography on silica gel (eluting with chloroform:ethanol 99:1) to give the title compound (0.360 g, 72%). $^1$H NMR: $\delta_H$ [(CD$_3$)$_2$SO] 0.02 (6H, s, (CH$_3$)$_2$Si), 0.86 (9H, s, (CH$_3$)$_3$C), 1.21 (6H, m, (CH$_3$CH$_2$O)$_2$), 1.62 (5H, m, CHCH$_2$CH$_2$P), 3.44 (4H, m, CH$_2$ONH$_2$, CH$_2$OTBDMS), 3.95 (4H, m, (CH$_2$CH$_2$O)$_2$, 5.90 (2H, br.s, D$_2$O exchangeable, ONH$_2$) Found: C, 44.36; H, 8.53; N, 4.55%. C$_{11}$H$_{24}$O$_6$NP requires: C, 44.44; H, 8.14; N, 4.71%.

d) 4-Chloro-6-2-(t-butyldimethylsilyloxymethyl)-4-(diethoxyphosphoryl)butoxyamino]-5-formamidopyrimidine 4,6-Dichloro-5-formamidopyrimidine (0.175 g, 0.91 mmol), diethyl 3-(t-butyldimethylsilyloxymethyl)-4-(aminooxy)butylphosphonate (0.260 g, 0.7 mmol) and N,N-diisopropylethylamine (0.317 ml, 1.83 mmol) were dissolved in diglyme (15 ml) and the mixture was stirred at 100° C. for 2.5 hours. The reaction mixture was allowed to cool and the solvent was evaporatd under reduced pressure. The residue was redissolved in diethyl ether and the solution was stirred at 0° C. for 30 minutes. N,N-diisopropylethylamine hydrochloride was filtered off, washed with diethyl ether and the combined filtrates were evaporated to dryness. The product was purified by column chromatography on silica gel (eluting with chloroform:ethanol 97:3) to give the title compound (0.260 g, 73%). $^1$H NMR: $\delta_H$ [(CD$_2$)$_2$SO] 0.034 (6H, s, (CH$_3$)$_2$Si), 0.86 (9H, s, (CH$_3$)$_3$C), 1.21 (6H, t, (OCH$_2$CH$_3$)$_2$, 1.62 (2H, m, CH$_2$CH$_2$P), 1.87 (3H, m, CHCH$_2$CH$_2$P), 3.62 (2H, m, CH$_2$OTBDMS), 3.91 (6H, m, CH$_2$ON, (OCH$_2$CH$_3$)$_2$), 8.15 (1H, s, H-2), 8.25 (1H, br.s, NHCHO), 9.5 (1H, br.s, D$_2$O exchangeable, NHOCH$_2$), 10.2 (1H, br.s, D$_2$O exchangeable, NHCHO).

e) 6-Chloro-9-[2-(t-butyldimethylsilyloxymethyl)-4-(diethoxyphosphoryl)butoxy]purine 4-Chloro-6-[2-(t-butyldimethylsilyloxymethyl)-4-(diethoxyphosphoryl)butoxyamino-5-formamidopyrimidine (0.210 g, 0.4 mmol) was dissolved in diethoxymethyl acetate (5 ml) and the resulting solution was stirred at 120° C. for 24 hours. The reaction mixture was then allowed to cool, and excess diethoxymethyl acetate was removed under reduced pressure. The residue was dissolved in 2M methanolic ammonia solution (5 ml) and stirred at 23° C. for 10 minutes. The solvents were evaporated under reduced pressure and the product was purified by column chromatography on silica gel (eluting with chloroform:ethanol 99:1) to yield the title compound (0.160 g, 79%). $^1$H NMR: $\delta_H$ [(CD$_3$)$_2$SO] 0.04 (6H, s, (CH$_3$)$_2$Si), 0.83 (9H, s, (CH$_3$)$_2$C), 1.22 (6H, t, J=7 Hz, (OCH$_2$CH$_3$)$_2$), 1.66 (2H, m, CH$_2$CH$_2$P), 1.84 (2H, m, CH$_2$P), 2.02 (1H, m, CHCH$_2$CH$_2$P), 3.71 (2H, m, CH$_2$OTBDMS), 3.98 (4H, m, (OCH$_2$CH$_3$), 4.43 (2H, m, NOCH$_2$), 8.8 (1H, s, H-2), 9.01 (1H, s, H-8). Found: C, 46.60; H, 7.69; N, 10.32%. C$_{20}$H$_{36}$N$_4$O$_5$PSiCl 0.6 H$_2$O requires: C, 46.38; H, 7.24; N, 10.81%.

f) 9-2-(t-butyldimethylsilyloxymethyl)-4-(diethoxyphosphoryl)butoxy]adenine

6-Chloro-9-[2-(t-butyldimethylsilyloxymethyl)-4-(diethoxyphosphoryl)butoxy]purine (0.130 g, 0.26 mmol) was dissolved in ethanolic ammonia solution (10 ml) and the resulting reaction mixture was kept at 110° C. for 4 hours. The solution was then allowed to cool, the solvent was evaporated and the residue chromatographed on silica gel (eluting with chloroform:ethanol 95:5) to yield the title compound (0.160 g, 85%). $^1$H NMR: $\delta_H$ [(CD$_3$)$_2$SO] 0.03 (3H, s, CHSiCH$_3$), 0.04 (3H, s, CH$_3$SiCH$_3$), 0.84 (9H, s, (CH$_3$)$_3$C), 1.22 (6H, t, J=7 Hz, (OCH$_2$CH$_3$)$_2$), 1.66 (2H, m, CH$_2$CH$_2$P), 1.9 (3H, m, CHCH$_2$CH$_2$P), 3.7 (2H, m, CH$_2$OTBDMS), 3.97 (4H, m, (OCH$_2$CH$_3$)$_2$), 4.32 (2H, m, NOCH$_2$), 7.36 (2H, br.s, D$_2$O exchangeable, NH$_2$), 8.12 (1H, s, H-2), 8.38 (1H, s, H-8). Found: C, 48.80; H, 7.94; N, 13.76%. C$_{20}$H$_{38}$N$_5$O$_5$PSi 0.6 H$_2$O requires: C, 48.20; H, 7.92; N, 14.05%.

g) 9-2-(Hydroxymethyl)-4-(diethoxyphosphoryl)butoxy]adenine

A solution of 9-[2-(t-butyldimethylsilyloxymethyl)-4-(diethoxyphosphoryl)butoxy]adenine (0.09 g, 0.185 mmol) in 80% acetic acid (15 ml) was stirred at 80° C. for 1 hour. The reaction mixture was then allowed to cool; the solvents were evaporated and the residue coevaporated with toluene (2×20 ml). The product was purified by column chromatography on silica gel (eluting with chloroform:ethanol 92:8) to yield the title compound (0.06 g, 88%). $^1$H NMR: $\delta_H$ [(CD$_3$)$_2$SO] 1.23 (6H, m, (OCH$_2$CH$_3$)$_2$, 1.67 (2H, m, CHCH$_2$CH$_2$P), 1.87 (3H, m, CHCH$_2$CH$_2$P), 3.52 (2H, m, CH$_2$OH), 3.98 (4H, m, (OCH$_2$CH$_3$)$_2$), 4.34 (2H, m, NOCH$_2$), 4.71 (1H, t, D$_2$O exchangeable CH$_2$OH), 7.36 (2H, br.s, D$_2$O exchangeable, NH$_2$), 8.13 (1H, s, H-2), 8.39 (1H, s, H-8).

EXAMPLE 1

9-(3-Phosphonopropoxy)guanine

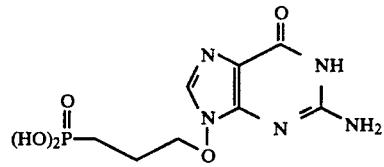

(E1)

To a solution of 9-[3-(diethoxyphosphoryl)propoxy]guanine (110 mg, 0.32 mmol) in dry DMF (2 ml) was added bromotrimethylsilane (0.25 ml, 1.91 mmol). The solution was left at ambient temperature for 24 hours, evaporated to dryness under reduced pressure, the residue dissolved in methanol and the solution evaporated to dryness again. The resulting solid was washed again with methanol. The solid was suspended in water (2 ml) and 0.880 NH$_3$ added to obtain a solution. The solution was passed through a column of Dowex 50W-X8(H) ion-exchange resin (previously washed with water) and the column eluted with water. The UV absorbing fractions were collected and evaporated to dryness to give the title compound as a white solid (45 mg, 50%), m.p. >300° C. UV: $\lambda$max (EtOH) 255 mm. IR: $\nu$max (KBr) 3700–2100 (broad), 1743, 1700, 1662, 1552, 1474, 1419, 1327, 1240, 1164, 1080, 1029, 1011, 969, 775, 694 cm$^{-1}$. $^1$H NMR: $\delta$H ((CD$_3$)$_2$SO) 1.6–1.9 (4H, m, CH$_2$CH$_2$P), 4.28 (2H, t, J=7 Hz, O—CH$_2$), 6.59 (2H, bs, D$_2$O exchangeable, NH$_2$), 7.92 (1H, s, H-8), 10.63 (1H, bs, D$_2$O exchangeable, NH), 2.5–4.5 (2H, broad, D$_2$O exchangeable, PO(OH)₂). C₈H₁₂N₅O₅P. 0.75 H₂O requires C, 31.74; H, 4.34; N, 23.14%. Found: C, 31.96; H, 4.13; N, 23.01%.

EXAMPLE 2

9-3-(Diethoxyphosphoryl)propoxy]guanine

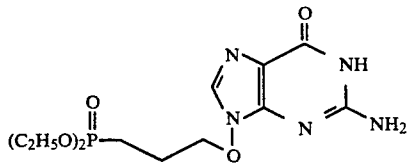

(E2)

A solution of 6-chloro-9-[3-(diethoxyphosphoryl)-propoxy]-2-formamidopurine (1.0 g, 2.5 mmol) in 80% formic acid (15 ml) was stirred and heated in an oil bath at 80° C. for 4.5 hours. After cooling, the solvent was removed under reduced pressure. The residue obtained was pre-absorbed onto silica gel using ethanol and then chromatographed using dichloromethane-methanol (90:10) as eluant. The title compound was obtained as a solid and recrystallised from ethanol (0.35 g, 40%). m.p. 203°-205° C. IR: υmax (KBr) 3330, 3158, 1695, 1646, 1600, 1475, 1389, 1243, 1165, 1055, 1027, 963 cm⁻¹. UV: λmax (EtOH) 255 nm (ε 14,100), λ shoulder, 276 nm (ε 9,000). ¹H NMR: δH ((CD₃)₂SO) 1.22 (6H, t, J=7 Hz, (OCH₂CH₃)₂), 1.75-2.0 (4H, m, CH₂CH₂P), 3.90-4.10 (4H, m, (OCH₂CH₃)₂), 4.30 (2H, t, J=6 Hz, N—OCH₂), 6.59 (2H, bs, D₂O exchangeable, NH₂), 7.95 (1H, s, H-8), 10.70 (1H, bs, D₂O exchangeable, NH). Found: C, 40.86; H, 5.70, N, 19.87%. C₁₂H₂₀N₅O₅P. 0.5 H₂O requires: C, 40.88; H, 5.95; N, 19.87%.

EXAMPLE 3

9-(4-Phosphonobutoxy)guanine

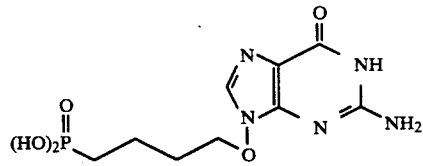

(E3)

9-[4-(Diethoxyphosphoryl)butoxy]guanine (0.12 g, 0.33 mmol) and bromotrimethylsilane (0.43 ml, 3.3 mmol) were dissolved in dimethylformamide (5 ml) and the reaction mixture was stirred at 23° C. for 3 hr. The solvent was evaporated under vacuum and the residue dissolved in methanol:water solution (9:1). The pH of the resulting solution was adjusted to 7.0 with diluted aq. ammonia and the solvents were evaporated to dryness. The product was purified by reversed phase chromatography (eluted with water) to give the title compound (65 mg, 64%) m.p. 208° C. (water), as its ammonium salt. ¹H NMR: δH ((CD₃)₂, SO+D₂O) 1.40 (2H, m, CH₂P), 1.68 (4H, br.s, CH₂CH₂), 4.21 (2H, m, NOCH₂), 7.89 (1H, s, H-8).

EXAMPLE 4

9-[4-(Diethoxyphosphoryl)butoxy]guanine

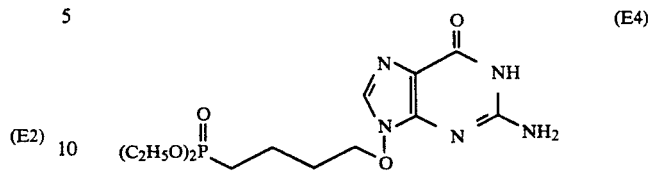

(E4)

A solution of 6-chloro-9-[4-(diethoxyphosphoryl)-butoxy]-2-formamidopurine (0.220 g, 0.54 mmol) in 80% formic acid (5 ml) was stirred at 80° C. for 5 hr. The solvent was evaporated under vacuum and the residue coevaporated with toluene (2×10 ml). The residue was chromatographed on silica gel (eluted with chloroform-ethanol 9:1) to give the title compound (0.148 g, 76%). ¹H NMR: δH ((CD₃)₂SO) 1.22 (6H, t, J=7 Hz, (OCH₂CH₃)₂), 1.64 (2H, m, CH₂P), 1.79 (4H, m, CH₂CH₂), 3.9 (4H, m, (OCH₂CH₃)₂), 4.26 (2H, t, NOCH₂), 6.67 (2H, br.s, D₂O exchangeable, NH₂), 7.96 (1H, s, H-8), 10.75 (1H, br.s, D₂O exchangeable, NH).

EXAMPLE 5

2,6-Diamino-9-(4-phosphonobutoxy)purine

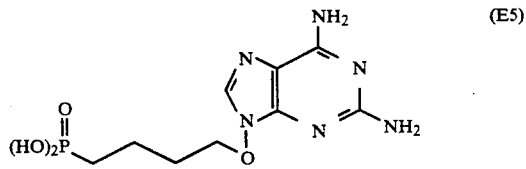

(E5)

2,6-Diamino-9-[4-(diethoxyphosphoryl)butoxy]purine (0.07 g, 0.2 mmol) and bromotrimethylsilane (0.26 ml, 2 mmol) were dissolved in dimethylformamide (3 ml) and the reaction mixture was stirred at 23° C. for 4 hr. The solvent was evaporated under vacuum and the residue dissolved in methanol-water solution (8:2). The material crystallised from the solution to give the title compound as colourless crystals (0.05 g, 84%), m.p. 295°-297° C. ¹H NMR: δH [(CD₃)₂SO+D₂O] 1.68 (6H, m, CH₂CH₂CH₂P), 4.31 (2H, t, J=6 Hz, NOCH₂), 8.35 (1H, s, H-8).

EXAMPLE 6

2,6-Diamino-9-4-(diethoxyphosphoryl)butoxy]purine

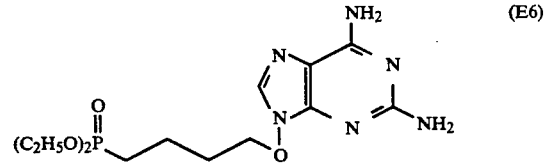

(E6)

6-Chloro-9-[4-(diethoxyphosphoryl)butoxy]-2-formamidopurine (170 mg, 0.42 mmol) was dissolved in ethanolic ammonia solution (10 ml) and the resulting reaction mixture was kept at 110° C. for 6 hr. The solution was then allowed to cool, the solvent was evaporated and the residue chromatographed on silica gel (eluted with chloroform-ethanol 9:1) to yield the title compound as colourless crystals (0.081 g, 54%); m.p. 143° C. (acetonitrile). ¹H NMR: δH [(CD₃)₂SO] 1.22 (6H, t, J=7 Hz, (OCH₂CH₃)₂), 1.74 (6H, m, CH₂CH₂CH₂P), 3.98 (4H, m, (OCH₂CH₃)2), 4.26 (2H, t, J=6 Hz, NOCH₂), 5.91 (2H, br.s, D₂O exchangeable, NH₂), 6.76 (2H, br.s, D₂O exchangeable, NH₂), 7.91 (1H, s, H-8).

EXAMPLE 7

9-(4-Phosphonobutoxy)adenine

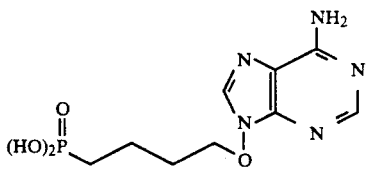
(E7)

9-[4-(Diethoxyphosphoryl)butoxy]adenine (0.165 g, 0.48 mmol) and bromotrimethylsilane (0.62 ml, 4.8 mmol) were dissolved in dimethylformamide (5 ml) and the reaction mixture was stirred at 23° C. for 90 min. The solvent was evaporated and the residue dissolved in methanol-water solution (9:1). The material crystallised from the solution to give the title compound as colourless crystals (96 mg, 70%), m.p. 265°–268° C. ¹H NMR: δH [CD₃)₂SO] 1.77 (6H, m, CH₂CH₂CH₂P), 4.45 (2H, t, J=6 Hz, NOCH₂), 7.46 (2H, br.s., D₂O exchangeable, NH₂), 8.24 (1H, s), 8.48 (1H, s).

EXAMPLE 8

9-4-(Diethoxyphosphoryl)butoxy]adenine

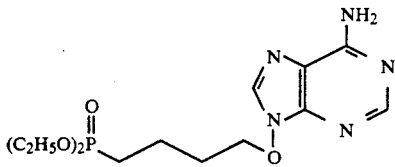
(E8)

6-Chloro-9-[4-(diethoxyphosphoryl)butoxy]purine (0.340 g, 0.94 mmol) was dissolved in ethanolic ammonia solution (10 ml) and the resulting reaction mixture was kept at 110° C. for 4 hr. The solution was then allowed to cool, the solvent was evaporated and the residue chromatographed on silica gel (eluted with chloroform-ethanol 9:1) to yield the title compound as colourless crystals (0.30 g, 93%), m.p. 110°–112° C. (acetonitrile). ¹H NMR: δH [(CD₃)₂SO] 1.22 (6H, t, J=7 Hz, (OCH₂CH₃)₂), 1.78 (6H, m, CH₂CH₂CH₂P), 3.98 (4H, m, (OCH₂CH₃)₂), 4.37 (2H, t, J=6 Hz, NOCH₂) 7.36(2H, br.s, D₂O exchangeable, NH₂), 8.14 (1H, s), 8.39 (1H, s).

EXAMPLE 9

9-(3-Phosphonopropoxy)adenine

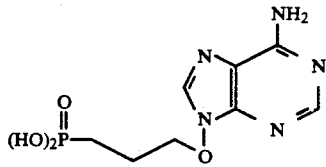
(E9)

To a solution of 9-[3-(diethoxyphosphoryl)propoxy]adenine (300 mg, 0.9 mmol) in dry dichloromethane (10 ml), was added bromotrimethylsilane (0.6 ml, 4.5 mmol). After 2 hours at ambient temperature, the solution was evaporated to dryness, the residue treated with methanol and the solution evaporated to dryness again. The solid residue was crystallised from methanol-acetone to afford 9-(3-phosphonopropoxy)adenine, hydrobromide salt, (80 mgs, 24%) m.p. 175°–180° C.. UV: λmax (MeOH) 259 (ε14,050) nm. IR: υmax (KBr) 1692, 1588, 1451, 1416, 1335, 1220, 1061, 1004, 952 cm⁻¹. ¹H NMR: δH [(CD₃)₂SO] 1.6-1.95 (4H, m, CH₂CH₂P), 4.47 (2H, t, J=6.5 Hz, N—OCH₂), 8.46 (1H, s), 8.76 (1H, s), 7.0-10.0 (5H, broad, D₂O exchangeable). Found: C, 27.29; H, 3.80; N, 19.64; Br, 21.52%. C₈H₁₃N₅O₄PBr requires: C, 27.13; H, 3.70; N, 19.78. Br, 22.50%.

EXAMPLE 10

9-3-(Diethoxyphosphoryl)propoxy]adenine

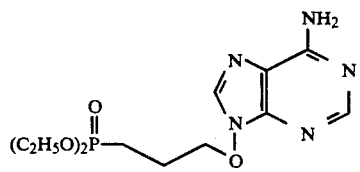
(E10)

A solution of 6-chloro-9-[3-(diethoxyphosphoryl)propoxy]purine (1.0 g, 2.8 mmol) in ethanol (15 ml) saturated with ammonia was heated in a sealed vessel at 100° C. for 3 hours. After cooling, the solvent was evaporated under reduced pressure and the residue chromatographed on silica gel (dichloromethane-methanol, 95:5 as eluant) to afford the title compound (0.5 g, 53%) m.p. 116°–117° C. (acetonitrile). UV: λmax (MeOH) 260 (ε 14,100)nm. IR: υmax (KBr) 3240, 3070, 1670, 1600, 1580, 1325, 1300, 1245, 1160, 1050, 1025, 965, 740 cm⁻¹. ¹H NMR: δH ((CD₃)₂SO) 1.21 (6H, t, J=7 Hz, (OCH₂CH₃)₂), 1.6-2.1 (4H, m, CH₂CH₂P), 4.00 (4H, m, (OCH₂CH₃)₂), 4.40 (2H, t, J=6.1 Hz, —OCH₂CH₂), 7.38 (2H, bs, D₂O exchangeable, NH₂), 8.14 (1H, s), 8.43 (1H, s).

EXAMPLE 11

9-3-Phosphono-1-(hydroxymethyl)propoxy]adenine

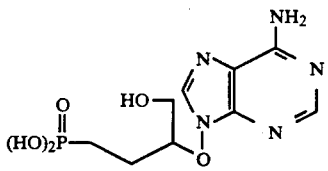
(E11)

Bromotrimethylsilyane (0.6 ml, 4.5 mmol) was added to a solution of 9-[3-(diethoxyphosphoryl)-1-(hydroxymethyl)propoxy]adenine (0.32 g, 0.9 mmol) and triethylamine (0.14 ml, 1 mmol) in dry dichloromethane (10 ml). After stirring at ambient temperature for 2 hours, the solvent was evaporated, the residue dissolved in methanol and then evaporated to dryness again. After repeating this methanol operation, the residue was crystallised using methanol-acetone and then recrystallised from methanol-water to give the title compound as a white crystalline solid m.p. 236°–237° C. (0.075 g, 28%). UV: λmax (EtOH) 260 nm (ε=14,500). IR: υmax (KBr) 3600–2400 (broad), 3251, 3160, 3108, 3072, 3063, 2948, 2932, 1707, 1607, 1407, 1348, 1340, 1299, 1232, 1205, 1162, 1110,1043, 1012, 971, 932, 901, 874, 774, 724 cm⁻¹. ¹H NMR: δH ((CD₃)₂SO) 1.7-2.0 (4H, m, —CH₂CH₂P), 3.5-3.6 (2H, m, —CH₂OH), 2.75–4.25 (3H, broad, D₂O exchangeable, OH, PO(OH)₂), 4.36

(1H, m, O-CHCH₂OH), 7.41 (2H, bs, D₂O exchangeable, NH₂), 8.15 (1H, s), 8.34 (1H, s). Found: C, 35.76; H, 4.58; N, 22.51% C₉H₁₄N₅O₅P requires: C, 35.65; H, 4.65; N, 23.09%.

EXAMPLE 12

9-3-(Diethoxyphosphoryl)-1-(hydroxymethyl)propoxy]adenine

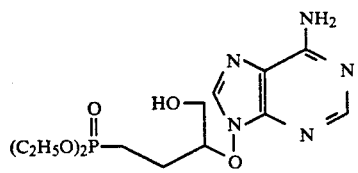
(E12)

A solution of 9-[1-(t-butyldimethylsilyloxymethyl)-3-(diethoxyphosphoryl)propoxy]adenine (1.05 g, 2.2 mmol) in 80% aqueous acetic acid (10 ml) was heated at 70° C. for 4 hours and t.l.c. indicated disappearence of starting material. After cooling to ambient temperature, the aqueous acetic acid was washed with hexane (3×10 ml), and then evaporated to dryness. The residue obtained was chromatographed on silica gel (dichloromethane-methanol (90:10) as eluant) to give the title compound (0.69 g). A sample was crystallised from ethanol-ether, m.p. 102.5°–104.5°. IR: υmax (KBr) 3317, 3142, 1672, 1647, 1600, 1582, 1468, 1413, 1323, 1300, 1212, 1199, 1170, 1098, 1059, 1031, 1009, 967, 901, 857, 824, 795 cm⁻¹. UV: λmax (MeOH) 260 nm (ε: 14,200). ¹H NMR: δH [(CD₃)₂SO]: 1.22 (6H, t, J=7 Hz, (OCH₂CH₃)₂), 1.7–2.25 (4H, m, CH₂CH₂P), 3.6 (2H, m, —CH₂OH), 3.99 (4H, m, (OCH₂CH₃)₂), 4.35 (1H, m, CH), 5.1 (1H, t, J=6 Hz, D₂O exchangeable, CH₂OH), 7.40 (2H, bs, D₂O exchangeable, NH₂), 8.15 (1H, s), 8.35 (1H, s). Found: C, 43.18; H, 6.10; N, 19.36%. C₁₃H₂₂N₅O₅P requires: C, 43.45; H, 6.17; N, 19.49%. m/z: C₁₃H₂₂N₅O₅P requires: 359.1359. Observed: 359.1372.

EXAMPLE 13

9-(2-Hydroxy-4-phosphonobutoxy)guanine

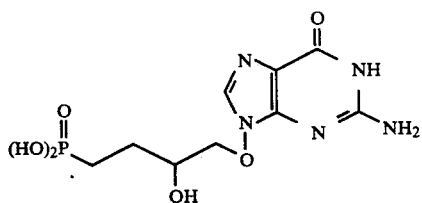
(E13)

A solution of 6-O-methyl-9-[2-hydroxy-4-(diethoxyphosphoryl)butoxy]guanine (80 mg, 0.2 mmol) and bromotrimethylsilane (0.4 ml, 0.3 mmol) in dry dimethylformamide (3 ml) was stirred at room temperature for 3 hours. The solvent was then evaporated and the residue coevaporated with dimethylformamide (2×5 ml) and methanol:water (9:1) solution (1×5ml). The product crystallised from water:methanol (9:1) to give the title compound (51 mg, 79%); mp>315° C. ¹H NMR: [(CD₃)₂SO] 1.64 (4H, m, CHCH₂CH₂P), 3.74 (1H, m, OCH₂CH₂CH₂), 4.12 (2H, m, OCH₂), 6.62 (2H, br.s, D₂O exchangeable NH₂), 7.91 (1H, s, H-8), 10.64 (1H, br.s, D₂O exchangeable, NH). Found: C, 34.25; H,4.37; N, 20.62%. C₉H₁₄N₅PO₆ requires: C, 33.87; H, 4.42; N, 21.94%.

EXAMPLE 14

9-2-Hydroxy-4-(diethoxyphosphoryl)butoxy]adenine

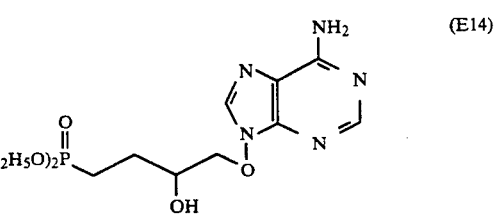
(E14)

A solution of 9-[2-(tert-butyldimethylsilyloxy)-4-(diethoxyphosphoryl)butoxy]adenine (0.150 g, 0.32 mmol) in 80% acetic acid (20 ml) was stirred at 80° C. for 27 hours. The solvent was then evaporated under reduced pressure and the residue coevaporated with toluene (3×20 ml). The product was purified by column chromatography on silica gel (eluting with chloromethane:ethanol 9:1) to give the title compound 57 mg, 50%). ¹H NMR: δH [(CD₃)₂SO] 1.21 (6H, t, (CH₃CH₂O)₂), 1.75 (4H, m, CHCH₂CH₂P), 3.78 (1H, m, CHCH₂CH₂P), 3.97 (4H, m, (CH₃CH₂O)₂), 4.25 (2H, m, OCH₂) 5.31 (1H, d, D₂O exchangeable, CHOH) 7.39 (2H, br. s, D₂O exchangeable NH₂), 8.15 (1H, s, H-2), 8.37 (1H, s, H-8).

EXAMPLE 15

9-(2-Hydroxy-4-phosphonobutoxy)adenine

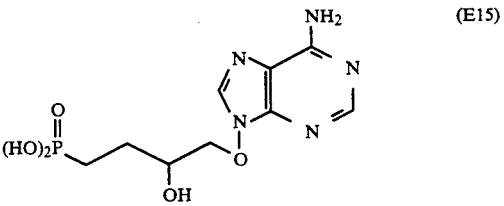
(E15)

A solution of 9-[2-hydroxy-4-(diethoxyphosphoryl)butoxy]adenine (0.50 g, 0.14 mmol) and bromotrimethylsilane (0.184 ml, 1.4 mmol) in dry dimethylformamide (3 ml) was stirred at room temperature for 3 hours. The solvent was then evaporated and the residue was coevaporated with dimethylformamide (2×5 ml) and methanol:water (9:1) solution. The product crystallised from water:methanol (9:1) solution to give the title compound (35 mg, 83%); m.p. 265°–267° C. ¹H NMR: δH [(CD₃)₂SO] 1.6 (4H, m, CH₃CH₂CH₂P), 3.8 (1H, m, CHCH₂CH₂P) 4.25 (2H, m, OCH₂) 7.41 (2H, br. s, D₂O exchangeable, NH₂), 8.16 (1H, s, H-2), 8.36 (1H, s, H-8). Found: C, 35.78; H, 4.52; N, 22.25%. C₉H₁₇N₅PO₅ requires: C, 35.65; H, 4.65; N, 23.1%.

EXAMPLE 16

9-[1-(Hydroxymethyl)-3-phosphonopropoxy]guanine

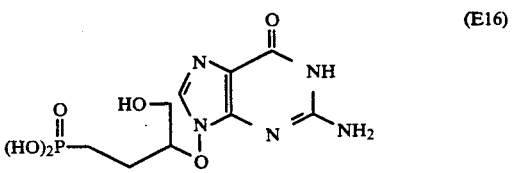
(E16)

A solution of 2-amino-9-[3-(diethoxyphosphoryl)-1-(hydroxymethyl)propoxy]-6-methoxypurine and bromotrimethylsilane (1.98 ml, 15 mmol) in dry dimethylformamide (5ml) was stirred at ambient temperature for 4 hours. The solvent was evaporated and the residue was coevaporated with methanol (5 ml) and acetone:water (1:1) solution. The product was crystallised from acetone:water (1:1) to give the title compound (90 mg, 56%) m.p. 177°–178° C. UV: λmax (H$_2$O) 254 (12400)nm. λsh(H$_2$O) 268 (9365)nm. IR: max (KBr) 3393, 3388, 3347, 3196, 3125, 2929, 2763, 2357, 1700, 1641, 1534, 1474, 1443, 1394, 1317, 1257, 1219, 1162, 1101, 1075, 992, 958, 818, 792, 772 cm$^{-1}$. $^1$H NMR $\delta_H$ [CD$_3$)$_2$SO] 1.67–1.94 (4H, m, CH$_2$CH$_2$P), 3.45–3.57 (2H, m, CH$_2$OH), 4.25–4.31 (1H, m, NOCH), 6.59 (2H, br.s, D$_2$O exchangeable NH$_2$), 7.88 (1H, s, H-8), 10.65 (1H, br.s, D$_2$O exchangeable NH), 2.75–6.25 (3H, broad, D$_2$O exchangeable OH, PO(OH)$_2$). Found: C, 33.21; H, 5.01; N, 21.42%. C$_9$H$_{14}$N$_5$O$_6$P 0.4 H$_2$O requires: C, 33.11; H, 4.56; N, 21.45%. m/z (FAB+ve ion, thioglycerol) MH+ 320.

EXAMPLE 17

9-(2-Hydroxy-3-phosphonopropoxy)guanine

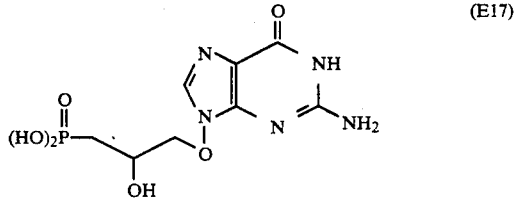
(E17)

A solution of 2-amino-6-methoxy-9-[2-hydroxy-3-(diethoxyphosphoryl)propoxy]purine (70 mg, 0.182 mmol) and bromotrimethylsilane (0.4 ml, 3 mmol) in dimethylformamide (3 ml) was stirred at 23° C. for 3 hours. The solvent was evaporated and the residue was coevaporated with dimethylformamide (2×5 ml) and methanol:water (9.1) solution (1×5 ml). Crystallization from water:methanol (9:1) gave the title compound (34 mg, 62%); m.p. 258° C.–260° C. $^1$H NMR: $\delta_H$ [(CD$_3$)$_2$SO] 1.80 (2H, m, PCH$_2$), 4.2 (3H, m, PCH$_2$CHCH$_2$), 6.62 (2H, br.s, D$_2$O exchangeable NH$_2$), 7.90 (1H, s, H-8), 10.64 (1H, br.s, D$_2$O exchangeable NH). Found: C, 31.34; H, 4.05; N, 22.61%. C$_8$H$_{12}$N$_5$O$_6$P requires: C, 31.48; H, 3.96; N, 22.95%.

EXAMPLE 18

9-[2-(Hydroxymethyl)-4-phosphonobutoxy]guanine

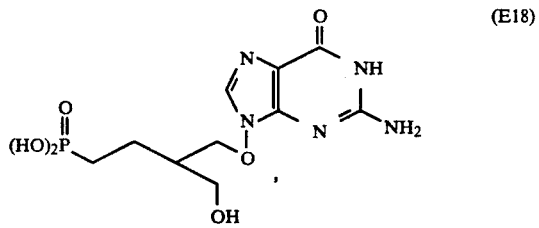
(E18)

9-[2-Hydroxymethyl)-4-(diethoxyphosphoryl)butoxy]guanine (50 mg, 0.128 mmol) and bromotrimethylsilane (1.28 ml, 0.169 mmol) were dissolved in dimethylformamide (5 ml) and the reaction mixture was stirred at 23° C. for 3 hours. The solvent was evaporated and the residue, after coevaporation with dimethylformamide (2×5 ml), was redissolved in methanol:water (9:1) solution. The pH of the resulting solution was adjusted to 7.0 with diluted aqueous ammonia and the solvents were evaporated to dryness. The product was purified by reverse phase chromatography (eluting with water) to give the title compound (30 mg, 70%). $^1$H NMR: $\delta_H$ [(CD$_3$)$_2$SO] 1.7 (5H, m, CHCH$_2$CH$_2$P), 3.45 (2H, m, CH$_2$OH), 4.24 (2H, m, NOCH$_2$), 6.93 (2H, br.s, D$_2$O exchangeable, NH$_2$), 7.9 (1H, s, H-8). Found C, 31.40; H, 5.62; N, 21.98%. C$_{10}$H$_{19}$N$_6$O$_6$P H$_2$O 0.2 HBr requires: C, 31.24; H, 5.55; N, 21.85%.

EXAMPLE 19

9-2-(Hydroxymethyl)-4-phosphonobutoxy]adenine

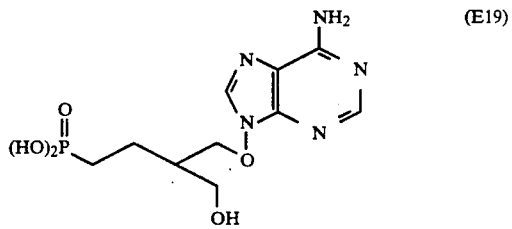
(E19)

A solution of 9-[2-(hydroxymethyl)-4-(diethoxyphosphoryl)butoxy]adenine (0.05 g, 0.134 mmol) and bromotrimethylsilane (0.18 g, 1.34 mmol) in dry dimethylformamide (3 ml) was stirred at 23° C. for 3 hours. The solvent was evaporated under reduced pressure and the residue coevaporated with dimethylformamide (2×5 ml). The product was dissolved in methanol:water (9:1) solution, the pH of the resulting solution adjusted to 7.0 with diluted aqueous ammonia, and the solution evaporated to dryness. The product was purified by reverse phase chromatography (eluting with water) to give the title compound (0.031 g, 73%). $^1$H NMR: $\delta_H$ [(CD$_3$)$_2$SO] 1.51 (4H, m, CH$_2$CH$_2$P), 1.89 (1H, m, CHCH$_2$CH$_2$P), 3.51 (2H, m, CH$_2$OH), 4.32 (2H, m, NOCH$_2$), 7.35 (2H, br.s, D$_2$O exchangeable, NH$_2$), 8.14 (1H, s, H-2), 8.41 (1H, s, H-8). Found: C, 32.60; H, 5.81; N, 22.90%. C$_{10}$H$_{19}$N$_6$O$_5$P H$_2$O 0.2 HBr requires: C, 32.59; H, 5.79; N, 22.80%.

EXAMPLE 20

2,6-Diamino-9-2-(hydroxymethyl)-4-phosphonobutoxy]purine

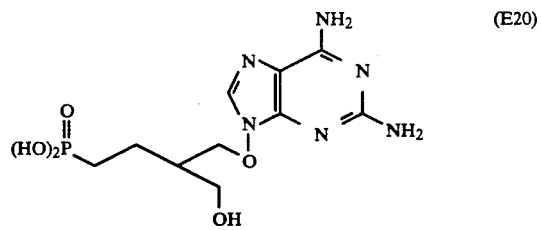
(E20)

2,6-Diamino-9-[2-(hydroxymethyl)-4-(diethoxyphosphoryl)butoxy]purine (0.03 g, 0.077 mmol) and bromotrimethylsilane (0.1 ml, 0.77 mmol) were dissolved in dimethylformamide (5 ml) and the reaction mixture was stirred at 23° C. for 3.5 hours. The solvent was evaporated and the residue coevaporated with dimethylformamide (2×3 ml). The resulting mixture was redissolved in methanol:water (9:1) solution, the pH of the solution adjusted to 7.0 with diluted aqueous ammonia and the solution evaporated to dryness. The product was purified by reversed phase chromatography (eluting with water) to give the title compound (2.0 mg, 74%). $^1$H NMR: $\delta_H$(D$_2$O) 1.57 (4H, m, CHC$\underline{H_2CH_2}$P), 2.01 (1H, m, C$\underline{H}$CH$_2$CH$_2$P), 3.8 (2H, m, C$\underline{H_2}$OH), 4.4 (2H, m, NOC$\underline{H_2}$), 8.08 (1H, s, H-8).

ANTIVIRAL ACTIVITY

1. Plaque Reduction Test for Herpes Simplex Viruses 1 and 2.

Cells (Vero or MRC-5) were grown to confluence in 24 well multi-dishes (well diameter=1.5 cm). The drained cell monolayers were each infected with approximately 50 infectious particles of herpes simplex virus 1 (HSV-1; strain HFEM) or herpes simplex virus 2 (HSV-2; strain MS) in 100 µl of phosphate-buffered saline. The virus was adsorbed for 1 hour at room temperature. After adsorption, residual inoculum was removed from each well and replaced with 0.5 ml of Eagle's MEM containing 5% newborn calf serum and 0.9% agarose (A37). Once the agarose had set, dilutions of the test compound, which had been prepared in Eagle's MEM (containing 5% newborn calf serum), were added, each well receiving 0.5 ml of liquid overlay. The test compound was diluted to give the following series of concentrations: 200, 60, 20, 6 . . . 0.06 µg/ml; final concentrations in the assay ranged, therefore, between 100 µg/ml and 0.03 µg/ml. The infected cultures were incubated at 37° C. in a humidified atmosphere of 5% CO$_2$ until plaques were clearly visible (2 or 3 days for Vero cells, usually 1 day for MRC-5 cells).

2. Plaque Reduction Test for Varicella Zoster-Virus

MRC-5 cells were grown to confluence in 24 well multi-dishes (well diameter=1.5 cm). The drained cell monolayers were each infected with approximately 50 infectious particles of varicella zoster virus (VZV; Ellen strain) in 100 µl of phosphate-buffered saline. The virus was adsorbed for 1 hour at room temperature. After adsorption, residual inoculum was removed from each well and replaced with 0.5 ml of Eagle's MEM containing 5% heat-inactivated foetal calf serum and 0.9% agarose (A37). Once the agarose had set, dilutions of the test compound, which had been prepared in Eagle's MEM (containing 5% heat-inactivated foetal calf serum), were added, each well receiving 0.5 ml of liquid overlay. The test compound was diluted to give the following series of concentrations: 200, 60, 20, 6 . . . 0.06 µg/ml; final concentrations in the assay ranged, therefore, between 100 µg/ml and 0.03 µg/ml. The infected cultures were incubated at 37° C. in a humidified atmosphere of 5% CO$_2$ until plaques were clearly visible (5 or 6 days).

Cultures from 1 and 2 were fixed in formal saline, the agarose overlays were carefully washed off, and then the cell monolayers were stained with carbol fuchsin. A stereo microscope was used to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurs was recorded.

3. CPE Inhibition Test (Established Monolayer) for Lentiviruses $3 \times 10^4$ sheep choroid plexus (SCP) cells were plated into individual wells of a 96 well microtitre plate in 100 µl of Eagle's MEM with Hanks' salts containing 10% heat inactivated foetal calf serum (FCS). When monolayers had become established (after 1 or 2 days growth) they were washed with 200 µl of maintenance medium (Eagle's MEM with Hanks' salts containing 0.5% FCS) and infected with 100 µl of visna virus (strain K184) in maintenance medium (30 TCID$_{50}$/ml). Test samples were diluted with maintenance medium in further 96 well microtitre plates over the range 200–0.06 µg/ml by 3-fold dilution steps. 100 µl of the diluted samples was then transferred directly onto virus-infected monolayers (final concentration range therefore 100–2 0.03 µg/ml) and incubated at in a humidified atmosphere containing 5% CO$_2$ until virus-induced CPE was maximal in the untreated virus-infected controls (usually 12–14 days). The plates were fixed with formal saline and stained with crystal violet. Virus-induced CPE was then scored microscopically and the minimum concentration of sample giving complete protection of the cell monolayers (MIC) determined.

| | Results | | | MIC (µg/ml) |
|---|---|---|---|---|
| | IC$_{50}$ (µg/ml) | | | |
| | Herpes Simplex virus | | Varicella | Visna |
| Example No. | Type 1 HFEM strain in vero cells | Type 2 MS strain in MRC-5 cells | Zoster virus Ellen strain in MRC-5 cells | Virus K184 strain in SCP cells |
| 1 | >100 | >100 | 73 | 3 |
| 3 | 62 | 23 | 6 | 1 |
| 5 | >100 | >100 | 17 | 10 |
| 7 | >100 | >100 | >100 | 100 |
| 11 | >100 | >100 | >100 | 30 |
| 13 | >100 | >100 | 29 | 10 |
| 15 | >100 | >100 | >100 | 100 |
| 16 | >100 | >100 | >100 | 100 |
| 18 | >100 | >100 | 5 | 1 |
| 20 | >100 | >100 | 17 | 10 |

TOXICITY

At concentrations up to 30 µg/ml;, none of the compounds were cytotoxic for the cell monolayers used in any of the tests.

We claim:

1. A compound of formula (I), or a pharmaceutically acceptable salt thereof:

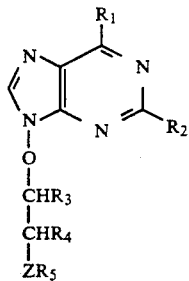 (I)

wherein
 R$_1$ is hydroxy or amino;
 R$_2$ is hydrogen or amino;
 R$_3$ is hydrogen, hydroxymethyl or acyloxymethyl;
 R$_4$ is hydrogen or (when R$_3$=H and Z is a bond or CH$_2$) hydroxy, hydroxymethyl or acyloxymethyl, C$_{1-7}$ alkanoyl or benzoyl optionally substituted by one, two or three groups or atoms selected from the group consisting of halogen, C$_{1-4}$ alkyl and C$_{1-4}$ alkoxy;
 Z is a bond, or a group CHR$_8$ wherein R$_8$ is hydrogen, or (when R$_3$=R$_4$=H), R$_8$ is hydroxy, acyloxy, hydroxymethyl or acyloxymethyl;
 R$_5$ is a group of formula:

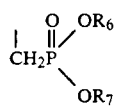

wherein
 R$_6$ and R$_7$ are independently selected from hydrogen, C$_{1-6}$ alkyl, a phenyl or a phenyl substituted by one, two or three groups or atoms selected from the group consisting of halogen, C$_{1-4}$ alkyl and C$_{1-4}$ alkoxy.

2. A compound according to claim 1 wherein R$_3$ is hydrogen, R$_4$ is hydrogen and Z is CHR$_8$, as defined in claim 1.

3. A compound according to claim 2 wherein R$_8$ is hydrogen or hydroxymethyl.

4. A compound according to claim 1 wherein R$_1$ is hydroxy and R$_2$ is amino.

5. A compound according to claim 1 wherein R$_1$ is amino and R$_2$ is hydrogen.

6. A compound selected from the group consisting of:
 9-(3-phosphonopropoxy)guanine;
 9-[3-(diethoxyphosphoryl)propoxy]guanine;
 9-(4-phosphonobutoxy)guanine;
 9-[4-(diethoxyphosphoryl)butoxy]guanine;
 2,6-diamino-9-(4-phosphonobutoxy)purine;
 2,6-diamino-9-[4-(diethoxyphosphoryl)butoxy]purine;
 9-(4-phosphonobutoxy)adenine;
 9-[4-(diethoxyphosphoryl)butoxy]adenine;
 9-(3-phosphonopropoxy)adenine;
 9-[3-(diethoxyphosphoryl)propoxy]adenine;
 9-[3-phosphono-1-(hydroxymethyl)propoxy]adenine;
 9-[3-(diethoxyphosphoryl)-1-(hydroxymethyl)propoxy]adenine;
 9-(2-hydroxy-4-phosphonobutoxy)guanine;
 9-[2-hydroxy-4-(diethoxyphosphoryl)butoxy]adenine;
 9-(2-hydroxy-4-phosphonobutoxy)adenine;
 9-(2-hydroxymethyl)-3-phosphonopropoxy)guanine;
 9-(2-hydroxy)-3-phosphonopropoxy)guanine;
 9-(2-hydroxymethyl)-4-phosphonobutoxy)guanine;
 9-(2-hydroxymethyl)-4-phosphonobutoxy)adenine; and
 2,6-diamino-9-(2-hydroxymethyl)-4-phosphonobutoxy)purine.

7. A pharmaceutical composition comprising a compound according to any one of claims 1 to 6, and a pharmaceutically acceptable carrier.

8. A method of treating in mammals viral infections selected from the group consisting of herpesvirus and lentivirus infections which comprises administering to said mammal an effective amount of a compound according to any one of claims 1 to 6.

* * * * *